United States Patent

Linz et al.

Patent Number: 5,563,268
Date of Patent: Oct. 8, 1996

[54] HETEROBIARYL DERIVATIVES

[75] Inventors: Guenter Linz, Mittelbiberach; Helmut Pieper, Biberach 1; Frank Himmelsbach, Mittelbiberach; Volkhard Austel, Biberach 1; Thomas Mueller, Biberach; Johannes Weisenberger, Biberach 1; Elke Seewaldt-Becker, Biberach, all of Germany

[73] Assignee: Dr. Karl Thomae GmbH, Biberach an der Riss, Germany

[21] Appl. No.: 375,084

[22] Filed: Jan. 19, 1995

Related U.S. Application Data

[62] Division of Ser. No. 961,135, Oct. 14, 1992, Pat. No. 5,418,233.

[30] Foreign Application Priority Data

Oct. 18, 1991 [DE] Germany .......................... 41 34 467.7

[51] Int. Cl.⁶ .................................................. C07D 403/02
[52] U.S. Cl. ........................ 544/238; 544/232; 544/243; 544/295; 544/337; 544/357; 544/360
[58] Field of Search ....................... 544/238, 295, 544/357, 232, 243, 337; 514/252

[56] References Cited

U.S. PATENT DOCUMENTS 5,276,049  1/1994  Himmelsbach et al. ................ 514/392

*Primary Examiner*—Richard L. Raymond
*Attorney, Agent, or Firm*—R. P. Raymond; M-E. M. Devlin; A. R. Stempel

[57] ABSTRACT

Heterobiaryl derivatives of the formula $$R_1NH-X_1-X_2-X_3-Y_1-Y_2-Y_3-Y_4-E \quad (I)$$

wherein $R_1$, $X_1$ to $X_3$ and $Y_1$ to $Y_4$ are as defined herein, the tautomers, stereoisomers and mixtures thereof, and the salts, particularly the physiologically acceptable salts, thereof with organic or inorganic acids or bases. The derivatives have valuable pharmacological properties, such as inhibiting cell-cell aggregation and cell-matrix interactions.

7 Claims, No Drawings

HETEROBIARYL DERIVATIVES

This is a division of application Ser. No. 07/961,135, filed Oct. 14, 1992, now U.S. Pat. No. 5,418,233.

The invention relates to heterobiaryl derivatives of general formula

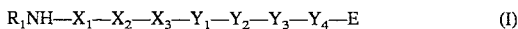

$$R_1NH-X_1-X_2-X_3-Y_1-Y_2-Y_3-Y_4-E \qquad (I)$$

with the exception of 2-guanidino-4-[3-[3-(methoxycarbonyl)propyl]-phenyl]-1,3-thiazole (see C.A. 103, 71307m (1985)) and 2-guanidino- 4-[6-[(methoxycarbonyl)-methyl]-pyrid-2-yl]-1,3-thiazole (see EP-A-417751), which are histamine receptor antagonists, the tautomers, stereoisomers, including mixtures thereof, and the salts thereof, more particularly the physiologically acceptable salts thereof with inorganic or organic acids or bases which have, inter alia, valuable pharmacological properties, preferably aggregation-inhibiting effects, pharmaceutical compositions containing these compounds and processes for preparing them.

In the above general formula I $R_1$ denotes a hydrogen atom, an alkyl, hydroxy, amino, alkoxycarbonyl, aralkoxycarbonyl, aryloxycarbonyl, alkylcarbonyl or arylcarbonyl group in which the alkyl and alkoxy moieties may each contain 1 to 4 carbon atoms, an alkenyloxycarbonyl group having a total of 4 to 6 carbon atoms, a phosphono, O-alkylphosphono, dialkylphosphoryl or R'—CO—O—(R"CH)—O—CO— group, wherein R' represents a $C_{1-5}$-alkyl group, a cycloalkyl, cycloalkylalkyl, aryl or aralkyl group and R" denotes a hydrogen atom, a $C_{1-5}$-alkyl group, a cycloalkyl or arylalkyl group, $X_1$ denotes a $C_{1-3}$-alkylene group, a —C(=NH)—, —C(=NH)—NH— or —C(=NH)—NH—CO— group, whilst the carbon atom of the —C(=NH)— group in the above-mentioned groups is linked to the nitrogen atom of the $R_1NH$— group, $X_2$ denotes a phenylene, pyridinylene, pyrazinylene, pyrimidinylene or pyridazinylene group, each of which may be mono- or disubstituted in the carbon skeleton by fluorine, chlorine, bromine or iodine atoms, by alkyl, aralkyl, aryl, pyridylalkyl, hydroxy, alkoxy, aralkoxy, pyridylalkoxy, alkylsulphenyl, alkylsulphinyl, alkylsulphonyl, amino, alkylamino, dialkylamino, alkylcarbonylamino, arylcarbonylamino, alkylsulphonylamino, arylsulphonylamino, aralkylamino, aminocarbonylalkyl, alkylaminocarbonylalkyl, dialkylaminocarbonylalkyl, $R_2$-, $R_2CO$-alkyl or $R_3CO$—$CHR_4$—$(CH_2)_1$—NHCO-alkyl groups, wherein the substituents may be identical or different and additionally in one of the above-mentioned 6-membered heteroaromatic groups containing one or two nitrogen atoms, one or two —N=CH— groups may be replaced by one or two —$NR_5$—CO— groups, wherein 1 represents the number 0 or 1, $R_2$ represents an azetidino, pyrrolidino, piperidino or hexamethyleneimino group, whilst the methylene group in the 4-position of a piperidino group may additionally be replaced by an —O—, —S—, —SO—, —$SO_2$—, —NH—, —N(alkyl)—, —N(CHO)—, —N(COalkyl)— or —N(COaryl)— group, $R_3$ denotes a hydroxy group or a $C_{1-5}$-alkoxy group wherein the alkoxy moiety in the 1-, 2- or 3-position may be substituted by an aryl or pyridyl group or in the 2- or 3-position by a pyrrolidino, piperidino, hexamethyleneimino, 2-oxo-1-pyrrolidinyl, morpholino or thiomorpholino group, $R_4$ denotes a hydrogen atom, a straight-chained or branched $C_{1-6}$-alkyl group which may be substituted by a hydroxy, mercapto, alkylmercapto, amino, $R_3CO$—, aminocarbonyl, phenyl, indolyl or imidazolyl group, whilst $R_3$ is as hereinbefore defined and the phenyl group may be substituted by a fluorine, chlorine or bromine atom or by a hydroxy or amino group, and $R_5$ denotes a hydrogen atom, an alkyl, aralkyl, aryl, pyridylalkyl, aminocarbonylalkyl, alkylaminocarbonylalkyl, dialkylaminocarbonylalkyl, $R_2CO$-alkyl or $R_3CO$—$CHR_4$—$(CH_2)_1$—NHCO-alkyl group, wherein 1, $R_2$, $R_3$ and $R_4$ are as hereinbefore defined, a thiophenylene, thiazolylene or thiadiazolylene group, $X_3$ has the meanings given for $X_2$ hereinbefore, with the proviso that $X_3$ does not represent a thiophenylene, thiazolylene or thiadiazolylene group and at least one of the groups $X_2$ or $X_3$ denotes one of the above-mentioned heteroaromatic groups, and $X_3$ denotes a 1,2,4-triazinylene group which may be substituted in the carbon skeleton by a fluorine, chlorine, bromine or iodine atom or by an alkyl, aralkyl, aryl, pyridylalkyl, hydroxy, alkoxy, aralkoxy, pyridylalkoxy, alkylsulphenyl, alkylsulphinyl, alkylsulphonyl, amino, alkylamino, dialkylamino, alkylcarbonylamino, arylcarbonylamino, alkylsulphonylamino, arylsulphonylamino, aralkylamino, aminocarbonylalkyl, alkylaminocarbonylalkyl, dialkylaminocarbonylalkyl, $R_2$-, $R_2CO$-alkyl or $R_3CO$—$CHR_4$—$(CH_2)_1$—NHCO-alkyl group, wherein 1, $R_2$, $R_3$ and $R_4$ are as hereinbefore defined and at the same time in a 1,2,4-triazinylene group mentioned above one or two —N=CH— groups may be replaced by one or two —$NR_5$—CO— groups, wherein $R_5$ is defined as hereinbefore and additionally in one of the rings containing an —$NR_5$—CO— group mentioned above in the definition of group $X_3$, $R_5$ may denote a bond to the group $X_2$ or, if $Y_1$ denotes a bond, $R_5$ may denote a bond to the group $Y_2$, $Y_1$ denotes a bond, an —O—, —S—, —SO—, —$SO_2$—, —CO—, —$NR_6$—, —$NR_6CO$—, —$CONR_6$—, —$SO_2NR_6$— or —$NR_6SO_2$— group, whilst $R_6$ denotes a hydrogen atom, a $C_{1-3}$-alkyl group or an aralkyl group, or an —$OCH_2CO$— group, if $Y_2$ denotes a bond and $Y_3$ is a piperidinylene group, $Y_2$ denotes a bond, a straight-chained or branched $C_{1-6}$-alkylene group, a straight-chained or branched alkenylene or alkynylene group each having 2 to 6 carbon atoms, whilst the double bond may not be linked directly to an oxygen, sulphur or phosphorus atom of the groups $Y_1$, $Y_3$ or E and the triple bond may not be directly linked to a heteroatom of the groups $Y_1$, $Y_3$ or E, or $Y_2$ may denote a $C_{3-7}$-cycloalkylene group or an arylene group optionally mono- or disubstituted by fluorine, chlorine, bromine or iodine atoms or by alkyl, hydroxy, alkoxy, alkylsulphenyl, alkylsulphinyl, alkylsulphonyl, amino, alkylcarbonylamino or alkylsulphonylamino groups, wherein the substituents may be identical or different, $Y_3$ denotes a bond, a —CO— or —$CONR_6$— group or, if a heteroatom of group $Y_1$ is not bound to the same carbon atom of group $Y_2$ as the group $Y_3$, $Y_3$ may denote an —O—, —S—, —SO—, —$SO_2$—, —$NR_6CO$— or —$NR_7$— group, whilst $R_7$ denotes a hydrogen atom, an alkyl, aralkyl, formyl, alkylcarbonyl, arylcarbonyl, aralkylcarbonyl, alkylsulphonyl, arylsulphonyl or aralkylsulphonyl group, a group of the formula

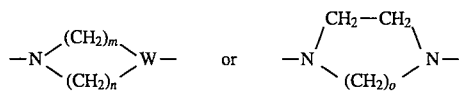

wherein

W denotes a >CH—, >C(OH)—, >CH—O—, >C=CH— or >C(CH$_2$COR$_3$)— group wherein $R_3$ is as hereinbefore defined, m and n in each case represent the numbers 1, 2 or 3 but m+n must represent the number 2, 3, 4, 5 or 6, and o denotes the number 2 or 3, whilst in the above-mentioned rings a methylene group may additionally be replaced by a carbonyl group or, if the methylene group is not adjacent to a nitrogen atom, it may be substituted by a hydroxy group, and generally an oxygen or sulphur atom of the group $Y_3$ may not directly follow an oxygen or sulphur atom or a CO— group of the group $Y_1$ and an oxygen atom or a sulphenyl or sulphinyl group of the group $Y_3$ may not directly follow a nitrogen atom of the group $Y_1$ and a CO— group of the group $Y_3$ may not directly follow an —O—, —S—, —SO— or —SO$_2$— group of the group $Y_1$, $Y_4$ denotes a bond, a straight-chained or branched $C_{1-4}$-alkylene group or an arylene group optionally mono- or disubstituted by fluorine, chlorine, bromine or iodine atoms or by alkyl, hydroxy, alkoxy, alkylsulphenyl, alkylsulphinyl, alkylsulphonyl, amino, alkylcarbonylamino or alkylsulphonylamino groups, whilst the substituents may be identical or different, and E denotes a sulpho, 5-tetrazolyl, phosphono, O-alkyl-phosphono, dialkylphosphoryl, R'—CO—O—(R"CH)—O—CO—, R'"CO— or R'O—CO—O—(R"CH)—O—CO— group, wherein R' and R" are as hereinbefore defined and R'" denotes a hydroxy group, a $C_{1-5}$-alkoxy group in which the alkoxy moiety may be substituted in the 1-, 2- or 3-position by an aryl or pyridyl group or in the 2- or 3-position by a pyrrolidino, piperidino, hexamethyleneimino, 2-oxo-1-pyrrolidinyl, morpholino or thiomorpholino group, an arylalkenyloxy group having 3 or 4 carbon atoms in the alkenyl moiety, a cycloalkoxy or cycloalkylalkoxy group, and at least one of the groups $Y_1$, $Y_2$, $Y_3$ or $Y_4$ does not represent a bond and the group E may not directly follow a heteroatom of groups $Y_1$ or $Y_3$, whilst unless otherwise stated, the term "an aryl or arylene group" denotes a phenyl or phenylene group optionally mono-, di- or trisubstituted by fluorine, chlorine, bromine or iodine atoms or by alkyl, trifluoromethyl, nitro, amino, alkylamino, dialkylamino, alkanoylamino, alkylsulphonylamino, aminosulphonyl, alkylaminosulphonyl, dialkylaminosulphonyl, hydroxy, alkoxy, carboxy, alkoxycarbonyl, aminocarbonyl, alkylaminocarbonyl, dialkylaminocarbonyl, alkylsulphenyl, alkylsulphinyl or alkylsulphonyl groups, wherein the substituents may be identical or different, and the above-mentioned alkyl, alkylene or alkoxy moieties may each contain 1 to 3 carbon atoms, the cycloalkyl and cycloalkoxy moieties may each contain 3 to 7 carbon atoms and the alkanoyl moieties may contain 1 to 4 carbon atoms.

However, preferred compounds of general formula I above are those wherein $R_1$ denotes a hydrogen atom, a $C_{1-4}$-alkyl group or an alkoxycarbonyl group having a total of 2 to 5 carbon atoms optionally phenyl-substituted in the alkoxy moiety, a phosphono group, an O-alkyl-phosphono or dialkylphosphoryl group wherein each alkyl moiety may contain 1 or 2 carbon atoms, or an R'—CO—O—(R"CH)—O—CO— group, wherein R' denotes a $C_{1-4}$-alkyl group or a $C_{5-6}$-cycloalkyl group and R" denotes a hydrogen atom or a methyl group, $X_1$ denotes a $C_{1-2}$-alkylene group or a —C(=NH)— group, $X_2$ denotes a phenylene, pyridinylene, pyrazinylene, pyrimidinylene or pyridazinylene group each of which may be substituted in the carbon skeleton by a fluorine, chlorine, bromine or iodine atom or by an alkyl, amino, hydroxy, alkoxy, pyrrolidino, piperidino, morpholino, thiomorpholino or N-acetylpiperazino group and wherein the alkyl or alkoxy moiety may contain 1 or 2 carbon atoms, or a thiazolylene group, $X_3$ has the meanings given for $X_2$ hereinbefore with the proviso that $X_3$ does not represent a thiazolylene group and at least one of the groups $X_2$ or $X_3$ denotes one of the above-mentioned heteroaromatic groups, and $X_3$ denotes a 1,2,4-triazinylene group, whilst in the heteroaromatic rings mentioned in the definition of the group $X_3$ hereinbefore, one or two —N=CH— groups may simultaneously be replaced by one or two —NR$_5$—CO— groups, wherein $R_5$ denotes a hydrogen atom, an alkyl, phenyl, benzyl, aminocarbonylalkyl, alkylaminocarbonyl-alkyl, dialkylaminocarbonylalkyl, R$_2$CO-alkyl or R$_3$CO—CHR$_4$—NHCO-alkyl group wherein the alkyl moiety may contain 1 to 3 carbon atoms, $R_2$ denotes a pyrrolidino, piperidino or hexamethyleneimino group wherein the methylene group in the 4-position of a piperidino group may additionally be replaced by an —O—, —S—, —NH—, —N(methyl)—, —NHCO— or —N(COCH$_3$)— group, and $R_5$ additionally, in one of the rings containing an —NR$_5$CO— group mentioned in the definition of the group $X_3$, denotes a bond to the group $X_2$ or, if $Y_1$ is a bond, to the group $Y_2$, $R_3$ denotes a hydroxy group or a $C_{1-5}$-alkoxy group wherein the alkoxy moiety may be substituted in the 1- or 2-position by an aryl or pyridyl group or in the 2-position by a morpholino or thiomorpholino group, and $R_4$ denotes a $C_{1-4}$-alkyl group which may be substituted in the 1- or 2-position by a phenyl or R$_3$CO— group, wherein $R_3$ is as hereinbefore defined and the phenyl group may be substituted by a chlorine or bromine atom or by a hydroxy or amino group, $Y_1$ denotes a bond, an —O—, —CO—, —NH—, —NCH$_3$—, —CONH—, —CONCH$_3$— or —SO$_2$NH— group or an —OCH$_2$CO— group if $Y_2$ denotes a bond and $Y_3$ denotes a piperidinylene group, $Y_2$ denotes a bond, a straight-chained or branched $C_{1-6}$-alkylene group, a straight-chained or branched $C_{2-6}$-alkenylene group, in which the double bond may not be directly connected to an oxygen, sulphur or phosphorus atom of the groups $Y_1$, $Y_3$ or E, a cyclohexylene group or a phenylene group optionally substituted by a fluorine, chlorine or bromine atom or by a methyl group, $Y_3$ denotes a bond, a —CO—, —CONH— or —CONCH$_3$— group or, if a heteroatom of the group $Y_1$ is not bound to the same carbon atom of the group $Y_2$ as the group $Y_3$, $Y_3$ may also denote an —O—, —NH—, —N(COCH$_3$)—, —N(benzoyl)— or —N(SO$_2$CH$_3$)— group, a group of the formula

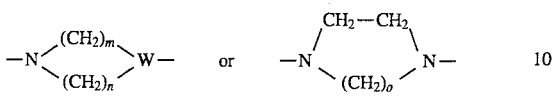

wherein

W denotes a >CH—, >C(OH)—, >CH—O—, >C=CH— or >C(CH$_2$COR$_3$)— group, wherein R$_3$ is defined as hereinbefore, m and n each represent the numbers 1, 2 or 3, but m+n must represent the number 3 or 4, and o denotes the number 2, whilst in the above-mentioned rings a methylene group may additionally be replaced by a carbonyl group or, if the methylene group is not adjacent to a nitrogen atom, it may be substituted by a hydroxy group, and generally an oxygen atom of the group $Y_3$ may not directly follow an oxygen atom or a CO group of the group $Y_1$ and an oxygen atom of the group $Y_3$ may not directly follow a nitrogen atom of the group $Y_1$ and a CO group of the group $Y_3$ may not directly follow an —O— group of the group $Y_1$, $Y_4$ denotes a bond, a straight-chained or branched C$_{1-4}$-alkylene group or a phenylene group optionally substituted by a fluorine, chlorine or bromine atom or by a methyl group and E denotes a sulpho, 5-tetrazolyl, phosphono, O-methylphosphono, R'—CO—O—(R"CH)—O—CO—, —R'''CO— or R'O—CO—O—(R"CH)—O—CO— group, wherein R' and R" are as hereinbefore defined and R''' denotes a hydroxy group, a C$_{1-5}$-alkoxy group in which the alkoxy moiety may be substituted in the 1- or 2-position by a phenyl or pyridyl group or in the 2- or 3-position by a pyrrolidino, piperidino, hexamethyleneimino, morpholino or thiomorpholino group, a C$_{4-7}$-cycloalkoxy group, a cycloalkylalkoxy group having 4 to 7 carbon atoms in the cycloalkyl moiety and 1 to 3 carbon atoms in the alkoxy moiety, or a phenylallyloxy group, and at least one of the groups $Y_1$, $Y_2$, $Y_3$ or $Y_4$ does not represent a bond and the group E may not directly follow a heteroatom of groups $Y_1$ or $Y_3$, the tautomers, stereoisomers, mixtures and salts thereof.

However, particularly preferred compounds of the above general formula are those wherein R$_1$ denotes a hydrogen atom, a C$_{1-4}$-alkyl group, an alkoxycarbonyl group having a total of 2 to 5 carbon atoms, a benzyloxycarbonyl, dimethylphosphoryl, diethylphosphoryl or R'—CO—O—(R"CH)—O—CO— group, wherein R' denotes a methyl or ethyl group and R" denotes a hydrogen atom or a methyl group, X$_1$ denotes a methylene group or a —C(=NH)— group, X$_2$ denotes a phenylene, pyridinylene, pyrazinylene, pyrimidinylene or pyridazinylene group each of which may be substituted in the carbon skeleton by a fluorine, chlorine or bromine atom or by a methyl, hydroxy, methoxy, ethoxy, amino, dimethylamino, pyrrolidino, piperidino, morpholino, thiomorpholino or N-acetylpiperazino group, or a thiazolylene group, X$_3$ has the meanings given for X$_2$ hereinbefore with the proviso that X$_3$ does not represent a thiazolylene group and at least one of the groups X$_2$ or X$_3$ denotes one of the above-mentioned heteroaromatic groups, and X$_3$ denotes a 1,2,4-triazinylene group, whilst in the heteroaromatic rings mentioned hereinbefore in the definition of the group X$_3$, an —N=CH— group may simultaneously be replaced by an —NR$_5$—CO— group, wherein R$_5$ denotes a hydrogen atom, a methyl, ethyl, phenyl, benzyl, aminocarbonylmethyl, dimethylaminocarbonyl-methyl, R$_2$CO-methyl or R$_3$CO—CHR$_4$— NHCO-methyl group, wherein R$_2$ is a morpholino group, R$_3$ is a hydroxy group or a C$_{1-3}$-alkoxy group and R$_4$ denotes a methyl or benzyl group and R$_5$ may additionally represent, in a ring containing an —NR$_5$—CO— group mentioned hereinbefore in the definition of the group X$_3$, a bond to the group X$_2$ or, if $Y_1$ denotes a bond, to the group $Y_2$, $Y_1$ denotes a bond, an —O—, —CO—, —NH—, —NCH$_3$—, —CONH—, —CONCH$_3$— or —SO$_2$NH— group or an —OCH$_2$CO— group if $Y_2$ denotes a bond and $Y_3$ is a piperidinylene group, $Y_2$ denotes a bond, a straight-chained or branched C$_{1-6}$-alkylene group, a straight-chained or branched C$_{2-6}$-alkenylene group, wherein the double bond may not be directly linked to an oxygen, sulphur or phosphorus atom of the groups $Y_1$, $Y_3$ or E, or $Y_2$ represents a cyclohexylene or phenylene group, $Y_3$ denotes a bond, a —CO—, —CONH— or —CONCH$_3$— group or, if a heteroatom of group $Y_1$ is not bound to the same carbon atom of the group $Y_2$ as the group $Y_3$, $Y_3$ may also denote an —O—, —NH—, —N(COCH$_3$)—, —N(benzoyl)— or —N(SO$_2$CH$_3$)— group, a group of the formula

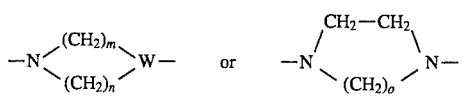

wherein

W represents a >CH—, >C(OH)—, >CH—O—, >C=CH— or >C(CH$_2$COR$_3$)— group, wherein R$_3$ is as hereinbefore defined, m and n each denote the numbers 1, 2 or 3, but m+n must represent the number 3 or 4, and o denotes the number 2, whilst in the above-mentioned rings a methylene group may additionally be replaced by a carbonyl group, and generally an oxygen atom of the group $Y_3$ may not directly follow an oxygen atom or a CO— group of the group $Y_1$ and an oxygen atom of the group $Y_3$ may not directly follow a nitrogen atom of the group $Y_1$ and a CO group of the group $Y_3$ may not directly follow an —O— group of the group $Y_1$, $Y_4$ denotes a bond, a straight-chained or branched C$_{1-4}$-alkylene group or a phenylene group and E denotes a sulpho, 5-tetrazolyl, phosphono, O-methylphosphono or R'''CO— group, wherein R''' denotes a hydroxy group, a C$_{1-4}$-alkoxy group, a cycloalkoxy or cycloalkoxymethoxy group each having 5 or 6 carbon atoms in the cycloalkoxy moiety, or a benzyloxy or pyridylmethoxy group, at least one of the groups $Y_1$, $Y_2$, $Y_3$ or $Y_4$ does not represent a bond and the group E may not directly follow a heteroatom of groups $Y_1$ or $Y_3$, the tautomers, stereoisomers and mixtures thereof and the salts thereof.

Particularly preferred compounds of general formula I above, however, are those wherein $R_1$ denotes a hydrogen atom or an alkoxycarbonyl group with a total of 2 or 3 carbon atoms, $X_1$ denotes a methylene group or a —C(=NH)— group, $X_2$ denotes a phenylene group, $X_3$ denotes a pyrimidinylene or pyridazinylene group, each of which may be substituted in the carbon skeleton by a methoxy or morpholino group, whilst in the above-mentioned heteroaromatic rings an —N=CH— group may simultaneously be replaced by an —NR_5—CO— group, whilst $R_5$ denotes a hydrogen atom or a methyl, benzyl or morpholinocarbonylmethyl group, $Y_1$ denotes a bond, an —O—, —CO—, —NH—, —NCH_3—, —CONH— or —CONCH_3— group, $Y_2$ denotes a bond, a straight-chained or branched $C_{1-4}$-alkylene group or a cyclohexylene or phenylene group, $Y_3$ denotes a bond, an —O— group or a group of the formula

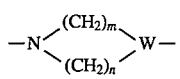

wherein

W denotes a >CH— or >CH—O— group, m and n each denote the numbers 1, 2 or 3, but m+n must represent the number 4, and generally an oxygen atom of the group $Y_3$ may not directly follow an oxygen atom or a CO group of the group $Y_1$ and an oxygen atom of the group $Y_3$ may not directly follow a nitrogen atom of the group $Y_1$ and a CO group of the group $Y_3$ may not directly follow an —O— group of the group $Y_1$, $Y_4$ denotes a bond, an alkylene group having 1 or 2 carbon atoms or a phenylene group and E denotes a carboxy group or an alkoxycarbonyl group having a total of 2 to 4 carbon atoms, wherein at least one of the groups $Y_1$, $Y_2$, $Y_3$ or $Y_4$ does not represent a bond and the group E may not directly follow a heteroatom of groups $Y_1$ or $Y_3$, but particularly those compounds of general formula I wherein $R_1$ denotes a hydrogen atom or an alkoxycarbonyl group having a total of 2 or 3 carbon atoms, $X_1$ is a methylene group or a —C(=NH)— group, $X_2$ is a phenylene group, $X_3$ is a pyrimidinylene group optionally substituted by a methoxy group, a pyridazinylene group optionally substituted by a methoxy or morpholino group, a pyrimidinylene or pyridazinylene group in which an —N=CH— group is replaced by an —NR_5—CO— group, wherein $R_5$ is a hydrogen atom or a methyl, benzyl or morpholinocarbonylmethyl group, $Y_1$ is a bond or a —CO—, —CONH— or —CONCH_3 group, $Y_2$ is a bond, a straight-chained $C_{3-4}$-alkylene group or a cyclohexylene group, $Y_3$ is a bond or a group of the formula

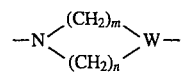

wherein

W is a >CH— group, m and n each denote the numbers 1, 2 or 3, but m+n must represent the number 4, $Y_4$ denotes a bond or a methylene group and E is a carboxy group or an alkoxycarbonyl group with a total of 2 or 3 carbon atoms, whilst at least one of the groups $Y_1$, $Y_2$, $Y_3$ or $Y_4$ does not denote a bond and the group E may not directly follow a heteroatom of the groups $Y_1$ or $Y_3$.

The following compounds are particularly preferred:

6-(4-amidinophenyl)-4-[(trans-4-carboxycyclohexyl)-aminocarbonyl]-2-methyl-(2H)-pyridazin-3-one, 6-(4-amidinophenyl)-4-[[trans-4-(methoxycarbonyl)-cyclohexyl]-aminocarbonyl]-2-methyl-(2H)-pyridazin-3-one, 6-[4-[N-(methoxycarbonyl)-amidino]-phenyl]-4-[[trans-4-(methoxycarbonyl)-cyclohexyl]-aminocarbonyl]-2-methyl-(2H)-pyridazin- 3-one, 6-[4-[N-(ethoxycarbonyl )-amidino]-phenyl]-4-[[trans-4-(methoxycarbonyl)-cyclohexyl]-aminocarbonyl]-2 -methyl-(2H)-pyridazin- 3-one, 2-(4-amidinophenyl)-5-[4-(carboxymethyl)-piperidinocarbonyl]- 4-methoxy-pyrimidine, 2-(4-amidinophenyl)-4-methoxy-5-[4-[(methoxycarbonyl)-methyl]-piperidinocarbonyl]-pyrimidine, 4-methoxy-2-[4-[N-(methoxycarbonyl)-amidino]-phenyl]-5-[4-[(methoxycarbonyl)-methyl]-piperidinocarbonyl]-pyrimidine, 6-(4-amidinophenyl)-4-[N-(trans-4-carboxycyclohexyl)-N-methylaminocarbonyl]- 2-methyl-(2H)-pyridazin-3-one, 6-(4-amidinophenyl)-4-[N-[trans-4-(methoxycarbonyl)-cyclohexyl]-N-methyl-aminocarbonyl]- 2-methyl-(2H)-pyridazin-3-one, 3-(4-amidinophenyl)-5-[(trans-4-carboxycyclohexyl)-aminocarbonyl]-pyridazine, 3-(4-amidinophenyl)-5-[[trans-4-(methoxycarbonyl)-cyclohexyl]-aminocarbonyl]-pyridazine, 6-(4-amidinophenyl)-4-[(trans-4-carboxycyclohexyl)-aminocarbonyl]- 2-[(morpholinocarbonyl)-methyl]-(2H)-pyridazin-3-one and 6-(4-amidinophenyl)-4-[[trans-4-(methoxycarbonyl)-cyclohexyl]-aminocarbonyl]-2-[(morpholinocarbonyl)-methyl] -(2H)-pyridazin-3-one, the tautomers and the salts thereof.

According to the invention the new compounds of general formula I may, for example, be obtained by the following methods known per se:

a) In order to prepare compounds of general formula I wherein E denotes a carboxy group:

Converting a compound of general formula $$R_1NH-X_1-X_2-X_3-Y_1-Y_2-Y_3-Y_4-E' \qquad (II)$$

wherein $R_1$, $X_1$ to $X_3$ and $Y_1$ to $Y_4$ are as hereinbefore defined and E', which is bound to a carbon atom, denotes a group which may be converted into a carboxy group by hydrolysis, treatment with acids, thermolysis or hydrogenolysis.

For example, functional derivatives of the carboxyl group such as the unsubstituted or substituted amides, esters, thioesters, trimethylsilyl esters, orthoesters, iminoesters, amidines or anhydrides, or the nitrile group may be converted by hydrolysis into a carboxyl group, esters with tertiary alcohols, e.g. the tert.butylester, may be converted by acid treatment or thermolysis into a carboxyl group and esters with aralkanols, e.g. the benzylester, may be converted by hydrogenolysis into a carboxyl group, and bis-(alkoxycarbonyl)methyl groups may be converted by hydrolysis or treatment with an acid into a bis(hydroxycarbonyl)methyl group which is subsequently decarboxylated.

The hydrolysis is appropriately carried out either in the presence of an acid such as hydrochloric acid, sulphuric acid, phosphoric acid, trichloroacetic acid or trifluoroacetic acid in the presence of a base such as lithium hydroxide, sodium hydroxide or potassium hydroxide in a suitable solvent such as water, methanol, water/methanol, ethanol, water/ethanol, water/isopropanol, water/tetrahydrofuran or water/dioxane at temperatures between $-10°$ C. and $120°$ C., e.g. at temperatures between ambient temperature and the boiling temperature of the reaction mixture. When hydrolysis is carried out in the presence of an organic acid such as trichloroacetic acid or trifluoroacetic acid, any alcoholic hydroxy groups present may simultaneously be converted into a corresponding acyloxy group such as the trifluoroacetoxy group.

If E' in a compound of formula II represents a cyano or aminocarbonyl group, these groups may also be converted into the carboxyl group with a nitrite, e.g. sodium nitrite, in the presence of an acid such as sulphuric acid, which may simultaneously also be used as solvent, at temperatures between $0°$ and $50°$ C.

If E' in a compound of formula II represents for example the tert.-butyloxycarbonyl group, the tert.-butyl group may also be cleaved, by treatment with an acid such as trifluoroacetic acid, formic acid, p-toluenesulphonic acid, sulphuric acid, phosphoric acid or polyphosphoric acid, optionally in an inert solvent such as methylene chloride, chloroform, benzene, toluene, tetrahydrofuran or dioxane, preferably at temperatures between $-10°$ C. and $120°$ C., e.g. at temperatures between $0°$ and $60°$ C., or thermally cleaved, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between $40°$ C. and $100°$ C.

If E' in a compound of formula II represents the benzyloxycarbonyl group, for example, the benzyl group may also be hydrogenolytically cleaved in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between $0°$ and $50°$ C., e.g. at ambient temperature, under a hydrogen pressure of 1 to 10 bar. During hydrogenolysis, other groups may be reduced at the same time, e.g. a nitro group may be reduced to the amino group, a benzyloxy group to the hydroxy group, or a benzyloxycarbonylamidino group may be converted into the amidino group.

b) In order to prepare compounds of general formula I wherein the $R_1NH—X_1—$ group denotes an amidino group wherein $R_1$ is a hydrogen atom or a hydroxy, alkyl or amino group:

Reacting a compound of general formula $$Z_1—C(=NH)—X_2—X_3—Y_1—Y_2—Y_3—Y_4—E \quad (III)$$

optionally formed in the reaction mixture, wherein $X_2$, $X_3$, $Y_1$ to $Y_4$ and E are as hereinbefore defined and $Z_1$ denotes an alkoxy or aralkoxy group such as a methoxy, ethoxy, n-propoxy, isopropoxy or benzyloxy group or an alkylthio or aralkylthio group such as a methylthio, ethylthio, n-propylthio or benzylthio group or an amino group, with an amine of general formula $$R_a—NH_2 \quad (IV)$$

wherein $R_a$ denotes a hydrogen atom or a hydroxy, alkyl or amino group, or with the acid addition salts thereof.

The reaction is conveniently carried out in a solvent such as methanol, ethanol, n-propanol, water, methanol/water, tetrahydrofuran or dioxane at temperatures between $0°$ and $150°$ C., preferably at temperatures between $20°$ and $120°$ C., with a corresponding free amine or with a corresponding acid addition salt such as ammonium carbonate or ammonium acetate.

A compound of general formula III, for example, is obtained by reacting a corresponding nitrile with a corresponding alcohol such as methanol, ethanol, n-propanol, isopropanol or benzyl alcohol in the presence of an acid such as hydrochloric acid or in the presence of a corresponding alkoxide such as sodium methoxide or sodium ethoxide or by reacting a corresponding amide with a trialkyloxonium salt such as triethyloxonium-tetrafluoroborate in a solvent such as methylene chloride, tetrahydrofuran or dioxane at temperatures between $-10°$ and $50°$ C., but preferably at temperatures between $0°$ and $20°$ C., or a corresponding nitrile with hydrogen sulphide, expediently in a solvent such as pyridine or dimethylformamide and in the presence of a base such as triethylamine with subsequent alkylation of the thioamide formed with a corresponding alkyl or aralkylhalide.

c) In order to prepare compounds of general formula I wherein the $R_1NH—X_1—$ group is an aminoalkyl group:

Reducing a compound of general formula $$NC—X_1·—X_2—X_3—Y_1—Y_2—Y_3—Y_4—E \quad (V)$$

wherein $X_2$, $X_3$, $Y_1$ to $Y_4$ and E are as hereinbefore defined and $X_1·$ denotes a bond or a $C_{1-2}$-alkylene group.

The reduction is preferably carried out in a suitable solvent such as methanol, methanol/water, methanol/ammonia, methanol/water/ammonia, methanol/hydrochloric acid, ethanol, ether, tetrahydrofuran, dioxane, dimethylformamide or glacial acetic acid in the presence of catalytically activated hydrogen, e.g. hydrogen in the presence of Raney nickel, platinum or palladium/charcoal, or in the presence of a metal hydride such as sodium borohydride or lithium borohydride at temperatures between $0°$ and $100°$ C., preferably at temperatures between $20°$ and $80°$ C.

d) In order to prepare compounds of general formula I wherein $R_1$ denotes an alkoxycarbonyl, aralkoxycarbonyl, aryloxycarbonyl, alkylcarbonyl or arylcarbonyl group in which the alkyl and alkoxy moieties may each contain 1 to 4 carbon atoms, an alkenyloxycarbonyl group having a total of 4 to 6 carbon atoms, a phosphono, O-alkyl-phosphono, dialkylphosphoryl or $R'—CO—O—(R"CH)—O—CO—$ group wherein $R'$ and $R''$ are as hereinbefore defined:

Reacting a compound of general formula $$H_2N—X_1—X_2—X_3—Y_1—Y_2—Y_3—Y_4—E \quad (VI)$$

wherein $X_1$ to $X_3$, $Y_1$ to $Y_4$ and E are as hereinbefore defined, with a compound of general formula $$Z_2\text{—}R_b \tag{VII}$$

wherein $R_b$ denotes an alkoxycarbonyl, aralkoxycarbonyl, aryloxycarbonyl, alkylcarbonyl or arylcarbonyl group in which the alkyl and alkoxy moieties may each contain 1 to 4 carbon atoms, an alkenyloxycarbonyl group with a total of 4 to 6 carbon atoms, an R'—CO—O—(R"CH)—O—CO— or dialkylphosphoryl group wherein R' and R" are as hereinbefore defined and, $Z_2$ denotes a nucleophilic leaving group such as a halogen atom, e.g. a chlorine or bromine atom, or an optionally substituted phenoxy group, e.g. a p-nitrophenoxy group, optionally with subsequent cleaving of one or two alkyl groups from a dialkylphosphoryl compound thus obtained.

The reaction is expediently carried out in a solvent or mixture of solvents such as water, tetrahydrofuran, tetrahydrofuran/water, dioxane, dioxane/water, methylene chloride, chloroform, ethyl acetate or dimethylformamide, appropriately in the presence of a base such as sodium carbonate, potassium carbonate or sodium hydroxide solution or in the presence of a tertiary organic base such as triethylamine, N-ethyl-diisopropylamine, N-methyl-morpholine or pyridine, which may simultaneously serve as solvent, at temperatures between −30° and 100° C., but preferably at temperatures between −10° and 80° C.

The cleaving of an alkyl group from a dialkylphosphoryl compound thus obtained is carried out, for example, with sodium iodide in a solvent such as acetone, ethylmethylketone, acetonitrile or dimethylformamide at temperatures between 40° and 150° C., but preferably at temperatures between 60° and 100° C.

The cleaving of both alkyl groups from a dialkylphosphoryl compound thus obtained is carried out, for example, using iodotrimethylsilane, bromotrimethylsilane or chlorotrimethylsilane/sodium iodide in a solvent such as methylene chloride, chloroform or acetonitrile at temperatures between 0° C. and the boiling temperature of the reaction mixture, but preferably at temperatures between 20° and 60° C.

e) In order to prepare compounds of general formula I wherein E denotes an R'''CO group where R''' is as hereinbefore defined:

Reacting a compound of general formula $$R_1NH\text{—}X_1\text{—}X_2\text{—}X_3\text{—}Y_1\text{—}Y_2\text{—}Y_3\text{—}Y_4\text{—}E'' \tag{VIII}$$

wherein $R_1$, $X_1$ to $X_3$ and $Y_1$ to $Y_4$ are as hereinbefore defined and E'' denotes a carboxy or alkoxycarbonyl group, with an alcohol of general formula $$HO\text{—}R''' \tag{IX}$$

wherein

R''' is as hereinbefore defined.

The reaction is conveniently carried out in a solvent or mixture of solvents such as methylene chloride, dimethylformamide, dimethylsulphoxide, benzene, chlorobenzene, tetrahydrofuran, benzene/tetrahydrofuran or dioxane, optionally in the presence of an acid such as hydrochloric acid or in the presence of a dehydrating agent, e.g. in the presence of isobutylchloroformate, thionylchloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, dimethylaminopyridine or 1-hydroxybenzotriazole, N,N'-carbonyldiimidazole or N,N'-thionyldiimidazole or triphenylphosphine/carbon tetrachloride, conveniently at temperatures between 0° and 150° C., preferably at temperatures between 0° and 50° C.

The reaction of a corresponding alkoxy compound of general formula VIII with an alcohol of general formula IX is preferably carried out in the alcohol in question as solvent optionally in the presence of another solvent such as methylene chloride or ether, preferably in the presence of an acid such as hydrochloric acid at temperatures between 0° and 100° C., preferably at temperatures between 20° and 80° C.

f) In order to prepare compounds of general formula I wherein $Y_1$ denotes a —CO— or —CONR$_6$— group:

Reacting a compound of general formula $$R_1NH\text{—}X_1\text{—}X_2\text{—}X_3\text{—}COOH \tag{X}$$

wherein $R_1$ and $X_1$ to $X_3$ are as hereinbefore defined, with a compound of general formula $$U\text{—}Y_2\text{—}Y_3\text{—}Y_4\text{—}E \tag{XI}$$

wherein $Y_2$ to $Y_4$ and E are as hereinbefore defined and, if $Y_2$ does not denote a bond, U represents an —NR$_7$— group wherein R$_7$ is as hereinbefore defined or, if $Y_3$ denotes one of the cyclic imino groups mentioned hereinbefore and $Y_2$ denotes a bond, U may also represent a hydrogen atom, or with a reactive derivative thereof.

The reaction is conveniently carried out in a solvent such as methylene chloride, chloroform, carbon tetrachloride, ether, tetrahydrofuran, dioxane, benzene, toluene, acetonitrile or dimethylformamide, optionally in the presence of an acid activating agent or a dehydrating agent, e.g. in the presence of ethylchloroformate, thionylchloride, phosphorus trichloride, phosphorus pentoxide, N,N'-dicyclohexylcarbodiimide, N,N'-dicyclohexyl-carbodiimide/N-hydroxysuccinimide, N,N'-carbonyldiimidazole or N,N'-thionyldiimidazole or triphenylphosphine/carbon tetrachloride, optionally in the presence of an inorganic base such as sodium carbonate or a tertiary organic base such as triethylamine or pyridine, which may simultaneously serve as solvent, at temperatures between −25° and 150° C., but preferably at temperatures between −10° C. and the boiling temperature of the solvent used. The acylation is, however, as described above, preferably carried out with a corresponding acid halide or acid anhydride, and may also be carried out without a solvent.

g) In order to prepare compounds of general formula I wherein E denotes an R'—CO—O—(R"CH)—O—CO—, R'O—CO—O—(R"CH)—O—CO— or R'''—CO— group, wherein R' to R''' are as hereinbefore defined:

Reacting a compound of general formula $$R_1NH\text{—}X_1\text{—}X_2\text{—}X_3\text{—}Y_1\text{—}Y_2\text{—}Y_3\text{—}Y_4\text{—}COOH \tag{XII}$$

wherein $R_1$, $X_2$ to $X_3$ and $Y_1$ to $Y_4$ are as hereinbefore defined, with a compound of general formula $$Z_3\text{—}R_c \tag{XIII}$$

wherein $R_c$ denotes an R'—CO—O—(R"CH)—, R'O—CO—O—(R"CH)— or R'''-group, wherein R' to R''' are as hereinbefore defined, and $Z_3$ denotes a nucleophilic leaving group such as a halogen atom, e.g. a chlorine or bromine atom.

The reaction is conveniently carried out in a solvent such as methylene chloride, tetrahydrofuran, dioxane, dimethylsulphoxide or dimethylformamide, optionally in the presence of a reaction accelerator such as sodium or potassium iodide and preferably in the presence of a base such as sodium carbonate, potassium carbonate or sodium hydroxide solution or in the presence of a tertiary organic base such as N-ethyl-diisopropylamine or N-methyl-morpholine, which may simultaneously serve as solvent, or optionally in the presence of silver carbonate or silver oxide at temperatures between −30° and 100° C., but preferably at temperatures between −10° and 80° C.

In the reactions described hereinbefore, any reactive groups present such as hydroxy, carboxy, amino, alkylamino or imino groups may optionally be protected during the reaction by conventional protecting groups which are split off again after the reaction.

Examples of protecting groups for a hydroxy group are the trimethylsilyl, acetyl, benzoyl, tert.-butyl, trityl, benzyl or tetrahydropyranyl group, examples of protecting groups for a carboxyl group are the trimethylsilyl, methyl, ethyl, tert.butyl, benzyl or tetrahydropyranyl group, and protecting groups for an amino, alkylamino or imino group include the acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, the phthalyl group.

The optional subsequent cleaving of a protecting group is preferably carried out by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide, or by ether splitting, e.g. in the presence of iodotrimethylsilane, at temperatures between 0° and 100° C., preferably at temperatures between 10° and 50° C.

However, a benzyl, methoxybenzyl or benzyloxycarbonyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of 1 to 7 bar, preferably of 3 to 5 bar.

A methoxybenzyl group may also be cleaved in the presence of an oxidising agent such as cerium(IV) ammonium nitrate in a solvent such as methylene chloride, acetonitrile or acetonitrile/water at temperatures between 0° and 50° C., but preferably at ambient temperature.

However, a 2,4-dimethoxybenzyl group is preferably split off in trifluoroacetic acid in the presence of anisole.

A tert.butyl or tert.butyloxycarbonyl group is preferably split off by treating with an acid such as trifluoroacetic acid or hydrochloric acid, optionally using a solvent such as methylene chloride, dioxane or ether.

A phthalyl group is preferably split off in the presence of hydrazine or a primary amine such as methylamine, ethylamine or n-butylamine in a solvent such as methanol, ethanol, isopropanol, toluene/water or dioxane at temperatures between 20° and 50° C.

Moreover, the compounds of general formula I may, as already indicated hereinbefore, be resolved into the enantiomers and/or diastereomers thereof. Cis/trans mixtures for example may be resolved into the cis- and trans-isomers and chiral compounds may be resolved into the enantiomers.

Thus, for example, the cis/trans mixtures obtained may be separated by chromatography into their cis and trans isomers, the compounds of general formula I obtained in the form of racemates may be separated by known methods (see Allinger N. L. and Eliel E. L. in "Topics in Stereochemistry", Vol. 6, Wiley Interscience, 1971) into their optical antipodes and compounds of general formula I having at least 2 asymmetric carbon atoms can be separated on the basis of their physical-chemical differences into their diastereomers by methods known per se, e.g. by chromatography and/or fractional crystallisation, and if these diastereomers are obtained in racemic form they may subsequently be separated into the enantiomers as mentioned above.

Enantiomer separation is preferably achieved by column separation on chiral phases or by recrystallisation from an optically active solvent or by reacting with an optically active substance which forms salts or derivatives such as esters or amides with the racemic compound, more particularly acids and their activated derivatives or alcohols, and separating the diastereomeric salt mixture obtained in this way, e.g. on the basis of different solubilities, whilst the free antipodes may be liberated from the pure diastereomeric salts by the action of suitable agents. Particularly common optically active acids are, for example, the D and L forms of tartaric acid or dibenzoyltartaric acid, di-o-tolyl-tartaric acid, malic acid, mandelic acid camphorsulphonic acid, glutamic acid, aspartic acid or quinic acid. An optically active alcohol might be, for example, (+)- or (−)-menthol and an optically active acyl group in amides might be (+) or (−)-menthyloxycarbonyl.

Moreover, the compounds of formula I obtained may be converted into the acid addition salts thereof, more particularly for pharmaceutical use the physiologically acceptable salts thereof with inorganic or organic acids. Examples of suitable acids include hydrochloric acid, hydrobromic acid, sulphuric acid, phosphoric acid, fumaric acid, succinic acid, lactic acid, citric acid, tartaric acid or maleic acid.

In addition, the new compounds of formula I thus obtained, should they contain a carboxyl group, may if desired subsequently be converted into the addition salts thereof with inorganic or organic bases, more particularly for pharmaceutical use into the physiologically acceptable addition salts thereof. Examples of suitable bases include sodium hydroxide, potassium hydroxide, ammonia, cyclohexylamine, ethanolamine, diethanolamine and triethanolamine.

The compounds used as starting materials are known from the literature in some cases or may be obtained by methods known from the literature as described in Examples I to XXIII.

As already mentioned hereinbefore, the new heterobiaryls of general formula I and the salts thereof, particularly the physiologically acceptable addition salts thereof with inorganic or organic acids or bases, have valuable properties. Thus, the compounds of general formula I wherein $R_1$ denotes a group which can optionally be cleaved in vivo, e.g. an alkoxycarbonyl group, and E denotes a carboxyl, phosphono, O-alkyl-phosphono or 5-tetrazolyl group or a group which may be converted in vivo into a carboxyl, sulpho, phosphono, O-alkyl-phosphono or tetrazolyl group, e.g. an alkoxy-substituted carbonyl group, not only have an antiinflammatory effect which inhibits the breakdown of bone but in particular antithrombotic, antiaggregatory and inhibitory effects on tumours or metastases.

By way of example, the compounds of general formula I were tested for their biological effects in the following way:
1. Fibrinogen binding to human thrombocytes Blood obtained by puncture of an antecubital vein is anticoagulated with trisodium citrate (final concentration: 13 mM) and centrifuged for 10 minutes at 170 *g. The supernatant platelet-rich plasma is placed on a Sepharose 2B column (Pharmacia) and eluted with a solution of 90 mM common salt, 14 mM trisodium citrate, 5 mM glucose and 50 mM tris(hydroxymethyl)aminomethane, adjusted to pH 7.4. The gel-filtered platelets (GFP) appearing in front of the plasma proteins are used for the binding tests.

50 µl of a 60 mM calcium chloride solution, 50 µl of a 0.6 mM adenosine diphosphate solution, 100 µl of substance solution or solvent and 50 µl of fibrinogen solution (containing 3 µg $^{125}$I-fibrinogen) are added to 750 µl of GFP and incubated for 20 minutes at ambient temperature. The non-specific binding is measured in the presence of 3 mg/ml of cold fibrinogen.

900 µl of the incubate are carefully pipetted onto 250 µl of silicon oil (AP 38: AR 20, 1:2 v/v, Wacker Chemie) in Eppendorf vessels and centrifuged for 2 minutes at 10,000 *g. The aqueous supernatant and some of the oil are removed, the tip of the vessel with the platelet pellet is cut off and the quantity of bound fibrinogen is measured in a gamma-counter. The concentration of substance which inhibits fibrinogen binding by 50% is calculated from a series of concentrations and given as the $IC_{50}$.

2. Antithrombotic activity

Method

The thrombocyte aggregation is measured using the Born and Cross method (J. Physiol. 170: 397 (1964)) in platelet-rich plasma taken from healthy volunteers. To inhibit coagulation the blood is mixed with 3.14% sodium citrate in a ratio by volume of 1:10.

Collagen-induced aggregation

The pattern of the decrease in optical density of the platelet suspension is photometrically measured and recorded after the addition of the aggregation-triggering substance. The rate of aggregation is concluded from the angle of inclination of the density curve. The point on the curve where there is maximum light transmittance is used to calculate the optical density.

The amount of collagen used is as small as possible but sufficient to produce an irreversible reaction curve. Standard commercial collagen produced by Hormonchemie of Munich is used. Before the addition of the collagen the plasma is incubated for 10 minutes with the substance at 37° C.

From the measurements obtained an $EC_{50}$ is determined graphically, indicating a 50% change in the optical density in terms of the inhibition of aggregation.

The Table which follows contains the results found:

| Substance (Example No.) | Fibrinogen binding test $ID_{50}$ [µM] | Inhibition of platelet aggregation $EC_{50}$ [µM] |
| --- | --- | --- |
| 1 | 0.13 | 0.42 |
| 1(3) | 0.20 | 0.39 |
| 1(4) | 0.037 | 0.54 |
| 1(7) | 4.40 | 12.00 |
| 1(8) | 1.70 | 39.00 |
| 1(11) | 0.58 | 1.20 |
| 1(14) | 0.033 | 0.10 |
| 1(16) | 0.055 | 0.16 |
| 1(20) | 0.057 | 0.29 |
| 1(18) | 0.033* | 0.31 |
| 1(21) | 0.062 | 0.32 |
| 1(30) | 0.033* | 0.10 |
| 2 | 1.90 | 0.36 |
| 2(1) | 3.20 | 1.90 |
| 2(15) | 52.00 | 5.20 |
| 2(17) | 2.30 | 1.30 |

-continued

| Substance (Example No.) | Fibrinogen binding test $ID_{50}$ [µM] | Inhibition of platelet aggregation $EC_{50}$ [µM] |
| --- | --- | --- |
| 3 | 2.20 | >300.00 |
| 4 | 0.37 | 0.79 |
| 5 | 6.20 | 3.00 |

*$^{125}$I fibrinogen was replaced by [$^{3}$H]-(3S,5S)-5-[(4'-amidino-4-biphenylyl)-oxymethyl]-3-carboxymethyl-2-pyrrolidone.

Moreover, when tested on rats, for example, the compound of Example 3 showed an antiaggregatory activity two hours after the oral administration of 10 mg/kg in an ex vivo test carried out with rat plasma in the presence of human thrombocytes.

The new compounds are well tolerated since the intravenous administration of 30 mg/kg of the compounds of Examples 1, 1(4), 1(16), 1(20), 3 and 4 to three mice did not cause any deaths.

In view of their inhibitory effect on cell-cell and cell-matrix interactions, the new heterobiaryls of general formula I and the physiologically acceptable addition salts thereof are suitable for combating or preventing diseases in which smaller or larger clumps of cells are produced or cell-matrix interactions are involved, e.g. in combating or preventing venous and arterial thrombosis, cerebro-vascular diseases, pulmonary embolisms, cardiac infarct, arteriosclerosis, osteoporosis and tumour metastasis and for treating genetically caused or acquired disorders of the interaction of cells with one another or with solid structures. They are also suitable as an accompanying therapy in thrombolysis with fibrinolytics or vascular interventions such as transluminal angioplasty or in the treatment of shock, psoriasis, diabetes and inflammation.

For combating or preventing the above-mentioned diseases, the dose is between 0.1 µg and 20 mg/kg of body weight, preferably 1 µg to 10 mg/kg of body weight, in up to 4 doses per day. For this purpose, the compounds of formula I prepared according to the invention may be formulated, optionally in conjunction with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof, to produce conventional galenic preparations such as plain or coated tablets, capsules, powders, suspensions, solutions, sprays or suppositories.

The Examples which follow are intended to illustrate the invention:

Preparation of the Starting Compounds

EXAMPLE I 3-(4-Cyanobenzoyl)-2-hydroxy-propionic acid 25 g of 4-cyano-acetophenone and 24 g of glyoxylic acid monohydrate are stirred for 5 hours at 95° C. in a water jet vacuum. A viscous oil is obtained which is dissolved in a mixture of saturated sodium hydrogen carbonate solution and ethyl acetate. The organic phase is separated off, the aqueous phase is acidified with 2N hydrochloric acid and extracted several times with ethyl acetate. The combined ethyl acetate phases are washed with water, dried and evaporated down. The residue is triturated with ether, suction filtered and further reacted as a crude product.

Yield: 18.2 g (48% of theory), $R_f$ value: 0.25 (silica gel; methylene chloride/methanol/acetic acid=8:2:0.2)

EXAMPLE II 6-(4-Cyanophenyl)-(2H)-pyridazin-3-one 19.2 g of 3-(4-cyanobenzoyl)-2-hydroxy-propionic acid and 20 ml of 80% hydrazine solution in 200 ml of acetic acid are refluxed for 2 hours. The mixture is left to cool, the precipitate is suction filtered and washed with acetic acid and ether.

Yield: 10.3 g (60% of theory), $R_f$ value: 0.32 (silica gel; methylene chloride/methanol=19:1)

EXAMPLE III

3-Chloro-6-(4-cyanophenyl)-pyridazine

A suspension of 27.6 g of 6-(4-cyanophenyl)-(2H)-pyridazin-3-one in 200 ml of phosphorusoxy chloride is refluxed for 2 hours. The reaction solution is introduced into 1 liter of water, the precipitate is suction filtered, washed with water and dried.

Yield: 25.7 g (85% of theory), Melting point: 237°–240° C., $R_f$ value: 0.75 (silica gel; methylene chloride/methanol=19:1)

The following compound is obtained analogously:
(1) 3-chloro-6-(4-cyanophenyl)-4-(ethoxycarbonyl)-pyridazine After the reaction solution has been stirred into water the aqueous phase is extracted with ethyl acetate. The organic phase is dried, evaporated down and the residue is chromatographed.

$R_f$ value: 0.37 (silica gel; cyclohexane/ethyl acetate=2:1)

EXAMPLE IV

Diethyl 2-(4-bromophenyl)-2-oxo-ethylmalonate 124 g of potassium tert.butoxide are added to a solution of 165 ml of diethylmalonate in 600 ml of dimethylformamide. Whilst cooling in a water bath 307 g of 4-bromophenacylbromide are added in batches whereupon the reaction solution heats up to about 70° C. It is stirred for 2 hours at ambient temperature, the reaction solution is poured into dilute saline solution and extracted with ethyl acetate. The organic phase is washed with water, dried over sodium sulphate and filtered over active charcoal. After the solvent has been removed using a rotary evaporator 398 g of a red oil are obtained which is further reacted without being purified.

$R_f$ value: 0.40 (silica gel; cyclohexane/ethyl acetate=5:1)

EXAMPLE V 6-(4-Bromophenyl)-4,5-dihydro-4-ethoxycarbonyl-(2H)-pyridazin-3-one To a solution of 398 g of diethyl 2-(4-bromophenyl)-2-oxo-ethylmalonate in 1.5 liters of glacial acetic acid are added 240 ml of 80% hydrazine solution and the mixture is refluxed for 2 hours. As the reaction solution cools a precipitate is formed which is suction filtered, washed with water and dried. In order to isolate further product, the mother liquor is mixed with water, the precipitate is suction filtered and recrystallised from glacial acetic acid.

Yield: 213 g (61% of theory), $R_f$ value: 0.31 (silica gel; cyclohexane/ethyl acetate=2:1)

EXAMPLE VI 6-(4-Bromophenyl)-4-ethoxycarbonyl-(2H)-pyridazin-3-one

To a suspension of 213 g of 6-(4-bromophenyl)-4,5-dihydro-4-ethoxycarbonyl-(2H)-pyridazin-3-one in 2.0 liters of glacial acetic acid is added dropwise a solution of 40 ml of bromine in 100 ml of glacial acetic acid and the mixture is stirred for 45 minutes at ambient temperature. It is diluted with 2.0 liters of water and excess bromine is destroyed with dilute sodium sulphite solution. The precipitate is suction filtered, washed with water and dried.

Yield: 206 g (97% of theory), $R_f$ value: 0.39 (silica gel; methylene chloride/methanol=15:1)

EXAMPLE VII 6-(4-Cyanophenyl)-4-ethoxycarbonyl-(2H)-pyridazin-3-one

To a solution of 24.6 g of 6-(4-bromophenyl)-4-ethoxycarbonyl-(2H)-pyridazin-3-one in 100 ml of dimethylformamide are added 6.9 g of copper(I)cyanide and the mixture is refluxed for 6 hours. The reaction solution is cooled and stirred into water. The precipitate is suction filtered and dried. 23 g of crude product are obtained which is further reacted without purification.

$R_f$ value: 0.39 (silica gel; methylene chloride/methanol=15:1)

EXAMPLE VIII 6-(4-Cyanophenyl)-4-ethoxycarbonyl-2-methyl-(2H)-pyridazin-3-one A suspension of 18 g of crude 6-(4-cyanophenyl)-4-ethoxycarbonyl-(2H)-pyridazin-3-one, 7.5 ml of methyliodide, 2.0 g of methyltrioctylammonium chloride in 200 ml of 2M potassium hydrogen carbonate solution, 500 ml of tetrahydrofuran and 1.6 liters of toluene is stirred for 16 hours at ambient temperature. 3 ml of methyliodide are added and the mixture is stirred for a further 4 hours. The precipitate is suction filtered and the filtrate is washed with water. The organic phase is dried over sodium sulphate, the solvent is evaporated off in vacuo and the crude product is chromatographed over silica gel.

Yield: 11.2 g (59% of theory), $R_f$ value: 0.49 (silica gel; methylene chloride/methanol=9:1)

The following compounds are obtained analogously:
(1) 2-benzyl-6-(4-cyanophenyl)-4-ethoxycarbonyl-(2H)-pyridazin-3-one
Benzylbromide is used.
Melting point: 151°–153° C. $R_f$ value: 0.55 (silica gel; methylene chloride/methanol=9:1)
(2) 6-(4-cyanophenyl)-4-ethoxycarbonyl-2-[(morpholinocarbonyl)methyl]-(2H)-pyridazin-3-one
1-chloroacetic acid morpholide is used.
Melting point: 186°–192° C. $R_f$ value: 0.57 (silica gel; methylene chloride/methanol=9:1)

EXAMPLE IX

4-Carboxy-6-(4-cyanophenyl)-2-methyl-(2H)-pyridazin-3-one

To a solution of 12.0 g of 6-(4-cyanophenyl)-4-ethoxycarbonyl-2-methyl-(2H)-pyridazin-3-one in 200 ml of tetrahydrofuran is added a solution of 7.14 g of lithium hydroxide monohydrate in 170 ml of water and the reaction is monitored by thin layer chromatography. After 1½ hours the mixture is acidified with 1N hydrochloric acid, the tetrahydrofuran is evaporated off in vacuo, the residue is suction filtered and dried.

Yield: 11.2 g (quant.), Melting point: 190°–194° C. $R_f$ value: 0.33 (silica gel; methylene chloride/methanol/conc. ammonia solution=4:1:0.25)

The following compounds are obtained analogously:
(1) 4-carboxy-6-(4-cyanophenyl)-(2H)-pyridazin-3-one
    Melting point: over 290° C.
(2) 2-(4-carbamoyl-phenyl)-5-carboxy-(3H)-pyrimidin-4-one
    $R_f$ value: 0.06 (silica gel; methylene chloride/methanol/conc. ammonia solution=2:1:0.25)

| Calculated: | C 55.60 | H 3.50 | N 16.21 |
|---|---|---|---|
| Found: | 55.45 | 3.53 | 16.36 |

(3) 4-[(trans-4-carboxycyclohexyl)-aminocarbonyl]-6-(4-cyanophenyl)-2-methyl-(2H)-pyridazin-3-one
    Melting point: 283°–286° C. $R_f$ value: 0.39 (silica gel; methylene chloride/methanol/=9:1)
(4) 4-carboxy-3-chloro-6-(4-cyanophenyl)-pyridazine
    Melting point: 208°–210° C. (decomp.) $R_f$ value: 0.74 (silica gel; methylene chloride/methanol/conc. ammonia solution=4:1:0.25)
(5) 2-benzyl-4-carboxy-6-(4-cyanophenyl)-(2H)-pyridazin-3-one
    Melting point: 254°–256° C. $R_f$ value: 0.29 (silica gel; methylene chloride/methanol/conc. ammonia solution=4:1:0.25)
(6) 4-carboxy-6-(4-cyanophenyl)-2-[(morpholinocarbonyl)-methyl]-(2H)-pyridazin-3-one
    Melting point: sintering from 215° C. $R_f$ value: 0.16 (silica gel; methylene chloride/methanol/conc. ammonia solution=4:1:0.25)
(7) 2-benzyl-4-[(trans-4-carboxycyclohexyl)-aminocarbonyl]-6-(4-cyanophenyl)-(2H)-pyridazin-3-one
    Melting point: 215°–218° C. $R_f$ value: 0.51 (silica gel; methylene chloride/methanol=9:1)

EXAMPLE X

6-(4-Cyanophenyl)-4-[[trans-4-(methoxycarbonyl)-cyclohexyl]aminocarbonyl]-2-methyl-(2H)-pyridazin-3-one A solution of 2.0 g of 4-carboxy-6-(4-cyanophenyl)-2-methyl-(2H)-pyridazin-3-one and 1.2 g of N-methylmorpholine in 160 ml of absolute tetrahydrofuran is cooled to −20° C. and mixed with 1.1 g of isobutyl-chloroformate. The mixture is stirred for one hour at −20° C., then cooled to −40° C. and a solution of 1.57 g of methyl trans-4-aminocyclohexanecarboxylate in 20 ml of absolute tetrahydrofuran is added. The cooling bath is taken away and the mixture is stirred for 3 hours at ambient temperature. The reaction solution is poured into 400 ml of 0.1N hydrochloric acid and the aqueous phase is extracted several times with ethyl acetate. Drying the organic phase over sodium sulphate and evaporating off the solvent yields a yellowish solid which is triturated with methanol. It is suction filtered and dried and 2.5 g (81% of theory) of product are obtained.

Melting point: 210°–215° C., $R_f$ value: 0.85 (silica gel; methylene chloride/methanol=9:1)

The following compounds are obtained analogously:
(1) 6-(4-cyanophenyl)-4-[[2-(ethoxycarbonyl)-ethyl]aminocarbonyl]- 2-methyl-(2H)-pyridazin-3-one
    β-alanine-ethylester-hydrochloride is used with one equivalent of N-methylmorpholine.
    Melting point: 132°–136° C., $R_f$ value: 0.39 (silica gel; methylene chloride/methanol=20:1)
(2) 6-(4-cyanophenyl)-4-[[3-(methoxycarbonyl)-propyl]-aminocarbonyl]-2-methyl-(2H)-pyridazin-3-one Ethyl 4-aminobutyrate-hydrochloride is used with one equivalent of N-methylmorpholine.
    Melting point: 130°–132° C., $R_f$ value: 0.42 (silica gel; methylene chloride/methanol=15:)
(3) 6-(4-cyanophenyl)-4-[[4-[(methoxycarbonyl)-methyl]-phenyl]-aminocarbonyl]-2-methyl-(2H)-pyridazin-3-one Freshly distilled methyl 4-aminophenyl-acetate is used.
    Melting point: 235°–238° C.,
(4) 6-(4-cyanophenyl)-4-[[cis-4-(methoxycarbonyl)-cyclohexyl]-aminocarbonyl]- 2-methyl-(2H)-pyridazin-3-one
    Melting point: 190°–192° C., $R_f$ value: 0.77 (silica gel; methylene chloride/methanol=15:1)
(5) 6-(4-cyanophenyl)-4-[[N-[trans-4-(methoxycarbonyl)-cyclohexyl]-N-methyl]-aminocarbonyl]-2-methyl-(2H)-pyridazin-3-one Methyl trans-4-(methylamino)-cyclohexane-carboxylate is used.
    Melting point: 228°–230° C., $R_f$ value: 0.48 (silica gel; methylene chloride/methanol=9:1)
(6) 3-chloro-6-(4-cyanophenyl)-4-[[trans-4-(methoxycarbonyl)-cyclohexyl]-aminocarbonyl]-pyridazine
    Melting point (after chromatography): 232°–234° C., $R_f$ value: 0.24 (silica gel; methylene chloride/methanol=20:1)
(7) 2-benzyl-6-(4-cyanophenyl)-4-[[trans-4-(methoxycarbonyl)-cyclohexyl]-aminocarbonyl]-(2H)-pyridazin-3-one
    Melting point: 217°–220° C., $R_f$ value: 0.64 (silica gel; methylene chloride/methanol=9:1)

EXAMPLE XI

6-(4-Cyanophenyl)-4-[(4-carboxybutyl)-aminocarbonyl]-2-methyl- (2H)-pyridazin-3-one A solution of 530 mg of 4-carboxy-6-(4-cyanophenyl)-2-methyl(2H)-pyridazin-3-one and 242 mg of N-methylmorpholine in 20 ml of absolute tetrahydrofuran is cooled to −15° C. and mixed with 273 mg of isobutylchloro-formate. The mixture is stirred for one hour at −15° C. Then a solution of 234 mg of 5-amino-valeric acid, 455 mg of N-methylmorpholine and 435 mg of trimethylsilylchloride in 50 ml of tetrahydrofuran stirred for 16 hours at ambient temperature is added. After 2 hours the cooling bath is removed and the mixture is stirred for 3 hours at ambient temperature. The reaction solution is poured into saturated sodium chloride solution, acidified with 2N hydrochloric acid and the aqueous phase is extracted several times with ethyl acetate. Drying the organic phase over sodium sulphate and evaporating off the solvent yields a yellowish solid which is triturated with a little methylene chloride. The mixture is suction filtered and dried and 600 mg (85% of theory) of the product are obtained.

Melting point: 194°–197° C., $R_f$ value: 0.51 (silica gel; methylene chloride/methanol=9:1)

The following compound is obtained analogously:
(1) 6-(4-cyanophenyl)-4-[(4-carboxybutyl )-aminocarbonyl]-(2H)-pyridazin- 3-one $R_f$ value: 0.30 (silica gel; methylene chloride/methanol=9:1)

EXAMPLE XII

4-Amidino-benzoic acid amide-hydrochloride

Dry HCl gas is passed for 2 hours through a solution of 17.5 g of 4-cyano-benzoic acid amide in 700 ml of methanol cooled in an ice/water bath (washing bottle containing concentrated sulphuric acid provided in front). The solution is stirred at ambient temperature and the conversion is monitored by thin layer chromatography. After the reaction is complete the reaction solution is evaporated down at a bath temperature of 25° to 35° C. in a rotary evaporator, the residue is dissolved in 300 ml of methanol and the solution is mixed with 10.0 g of ammonium carbonate with thorough stirring. The mixture is stirred for 16 hours at ambient temperature, the precipitate is removed by suction filtering, washed with a little water and dried in vacuo.

Yield: 8.5 g (35% of theory). By concentrating the filtrate and triturating the residue with a little water, suction filtering and drying, a further 8.8 g (37% of theory) of product can be obtained. Melting point: over 280° C., $R_f$ value: 0.09 (silica gel; methylene chloride/methanol/conc. ammonia solution=2:1:0.25)

EXAMPLE XIII

2-(4-Carbamoyl-phenyl)-5-ethoxycarbonyl-(3H)-pyrimidin-4-one

Under an inert gas atmosphere a solution of 1.8 g of sodium in 800 ml of absolute ethanol is prepared. At 0° C. 8.3 g of 4-amidino-benzoic acid amide-hydrochloride is added in small amounts. The suspension is stirred at 0° C. for 10 minutes. Then 8.7 g of diethylethoxy-methylene malonate are added. The mixture is stirred for 30 minutes at ambient temperature and refluxed for 2 hours. After a further 16 hours stirring at ambient temperature the precipitate is suction filtered and washed with ethanol. The residue is triturated with water, suction filtered again and dried.

Yield: 10.15 g (88% of theory), $R_f$ value: 0.78 (silica gel; methylene chloride/methanol/conc. ammonia solution= 2:1:0.25)

EXAMPLE XIV

1:1 Mixture of 5-carboxy-4-chloro-2-(4-cyanophenyl)-pyrimidine and 4-chloro-5-chloroformyl-2-(4-cyanophenyl)-pyrimidine A solution of 12.6 g of 2-(4-carbamoyl-phenyl)-5-carboxy-(3H)-pyrimidin- 4-one in 100 ml of phosphorus-oxychloride is refluxed for 4 hours. The mixture is left to cool and the reaction solution is poured in small amounts onto water whilst the temperature is maintained at between 60°–90° C. by the addition of ice. The precipitate is suction filtered and dried. 10.3 g of a 1:1 mixture of carboxylic acid and acid chloride is obtained which is further reacted as it is in Example XV.

EXAMPLE XV

4-Chloro-2-(4-cyanophenyl)-5-[4-[(methoxycarbonyl)-methyl]piperidinocarbonyl]-pyrimidine A solution of 7.0 g of the 1:1 mixture of 5-carboxy-4-chloro-2-( 4-cyanophenyl)-pyrimidine and 4-chloro-5-chloroformyl-2-(4-cyanophenyl)-pyrimidine (from Example XIV) in 60 ml of thionylchloride is refluxed for 3 hours. Excess thionylchloride is evaporated off, the residue is dissolved in dry tetrahydrofuran and evaporated down again. It is dissolved in 200 ml of dry tetrahydrofuran and 4.45 g of methyl piperidine-4-acetate hydrochloride are added. Then a solution of 10.5 ml of triethylamine in 25 ml of tetrahydrofuran is added dropwise whilst cooling in an ice/water bath and the mixture is stirred for 16 hours at ambient temperature. The suspension is acidified with 1N hydrochloric acid and the aqueous phase is extracted with ethyl acetate. The organic phase is evaporated down and the residue is purified by chromatography.

Yield: 5.95 g (65% of theory), $R_f$ value: 0.56 (silica gel; methylene chloride/methanol=15:1)

EXAMPLE XVI

2-(4-Cyanophenyl)-5-[4-[(methoxycarbonyl)-methyl]-piperidinocarbonyl]-(3H)- pyrimidin-4-one A solution of 2.0 g of 4-chloro-2-(4-cyanophenyl)-5-[4-[(methoxycarbonyl)-methyl]-piperidinocarbonyl]-pyrimidine and 4.1 g of sodium acetate in 150 ml of glacial acetic acid is refluxed for 24 hours. The glacial acetic acid is evaporated off and the residue is triturated with 200 ml of water. The precipitate is suction filtered and the solid is purified by chromatography over silica gel.

Yield: 0.85 g (45% of theory), $R_f$ value: 0.40 (silica gel; methylene chloride/methanol=15:1)

EXAMPLE XVII

2-(4-Cyanophenyl)-5-[4-[(methoxycarbonyl)-methyl]-piperidinocarbonyl]-pyrimidine 1.0 g of 5% palladium on calcium carbonate in 100 ml of dry methanol is prehydrogenated. 1.5 g of 4-chloro-2-(4-cyanophenyl)- 5-[4-[(methoxycarbonyl)-methyl]-piperidinocarbonyl]-pyrimidine and 0.28 g of calcium hydroxide are added and the mixture is hydrogenated for 1.5 hours at ambient temperature and atmospheric pressure. The insoluble components are filtered off, the filtrate is evaporated down and the residue is chromatographed over silica gel.

Yield: 650 mg (47% of theory), $R_f$ value: 0.46 (silica gel; ethyl acetate/cyclohexane=2:1)

The following compound is obtained analogously:
(1) 3-(4-cyanophenyl)-5-[[trans-4-(methoxycarbonyl)-cyclohexyl]-aminocarbonyl]-pyridazine $R_f$ value: 0.34 (silica gel; ethyl acetate/cyclohexane=2:1)

EXAMPLE XVIII

6-(4-Cyanophenyl)-3-[3-[(ethoxycarbonyl)-methyloxy]-piperidino]-pyridazine

A suspension of 1.50 g of 3-chloro-6-(4-cyanophenyl)-pyridazine, 1.90 g of 3-[(ethoxycarbonyl)-methyloxy]-piperidine and 1.70 g of potassium carbonate in 4 ml of dimethylsulphoxide is stirred for one hour at 130° C. The suspension is poured into water and the aqueous phase is extracted three times with ethyl acetate. Drying the ethyl acetate phase over sodium sulphate and evaporating off the solvent yields an oil which is chromatographed over silica gel.

Yield: 1.70 g (68% of theory) colourless oil, $R_f$ value: 0.42 (silica gel; cyclohexane/ethyl acetate=2:3)

The following compounds are obtained analogously:
(1) 6-(4-cyanophenyl)-3-[[trans-4-(methoxycarbonyl)-cyclohexyl]-amino]-pyridazine $R_f$ value: 0.20 (silica gel; methylene chloride/methanol= 100:1)
(2) 6-(4-cyanophenyl)-3-[[3-(methoxycarbonyl)-phenyl]-methylamino]-pyridazine $R_f$ value: 0.48 (silica gel; methylene chloride/methanol= 40:1)
(3) 6-(4-cyanophenyl)-3-[4-[2-(methoxycarbonyl)-ethyl]-phenyloxy]-pyridazine The mixture is heated to 80°–90° C. for 2.5 hours.

Melting point: 164°–167° C., $R_f$ value: 0.19 (silica gel; methylene chloride/methanol=100:1)
(4) 6-(4-cyanophenyl)-3-[4-[(methoxycarbonyl)-methyloxy]-phenyloxy]-pyridazine The mixture is heated to 80°–90° C. for 2.5 hours. The crude product is triturated with ethyl acetate and the precipitate is suction filtered and dried.

$R_f$ value: 0.45 (silica gel; methylene chloride/methanol= 20:1)
(5) 6-(4-cyanophenyl)-3-[[N-[trans-4-(methoxycarbonyl)-cyclohexyl]-N-methyl] -amino]-pyridazine $R_f$ value: 0.21 (silica gel; methylene chloride/methanol= 30:1)

EXAMPLE XIX 6-(4-Cyanophenyl)-3-[4-[2-(methoxycarbonyl)-ethyl]-phenylamino]-pyridazine 0.60 g of 3-chloro-6-(4-cyanophenyl)-pyridazine are heated to 140°–150° C. for 1.5 hours with 1.70 g of 4-[2-(methoxycarbonyl)ethyl]-aniline. The cooled melt is dissolved in methylene chloride and the organic phase is extracted with 1N sodium hydroxide solution. Drying the organic phase over sodium sulphate and evaporating off the solvent yields a solid which is chromatographed over silica gel.

Yield: 1.80 g (95% of theory), Melting point: 212°–217° C., $R_f$ value: 0.34 (silica gel; methylene chloride/methanol= 20:1)

EXAMPLE XX 6-(4-Cyanophenyl)-4-[[trans-4-(methoxycarbonyl)-cyclohexyl]-aminocarbonyl]-3-morpholino-pyridazine A solution of 1.0 g of 3-chloro-6-(4-cyanophenyl)-4-[[trans-4-(methoxycarbonyl)-cyclohexyl]-aminocarbonyl]-pyridazine in 10 ml of morpholine is refluxed for 2 hours. Excess morpholine is evaporated off, the residue is mixed with 0.5 N sodium hydroxide solution and the aqueous phase is extracted with methylene chloride. The organic phase is dried over sodium sulphate and evaporated down. 1.1 g of crude product are obtained which is chromatographed over silica gel.

Yield: 650 mg (49% of theory), Melting point: 269°–271° C., $R_f$ value: 0.29 (silica gel; methylene chloride/methanol= 20:1)

EXAMPLE XXI

Cis- and trans methyl 4-(N,N-dibenzylamino)-cyclohexylcarboxylate

A solution of 68.0 g of a cis/trans mixture of methyl 4-aminocyclohexyl-carboxylate, 154 g of benzylbromide and 156 g of N-ethyl-diisopropylamine in 300 ml of methanol are refluxed for 2 hours. The reaction solution is evaporated down. To the residue is added water followed by sufficient 1N sodium hydroxide solution to render the suspension alkaline. It is extracted several times with ethyl acetate, the organic phase is dried over sodium sulphate and the solvent is evaporated off. 130 g of an oil are obtained which is chromatographed with cyclohexane/ethyl acetate in the ratio 16:1 over silica gel.

Yield: 54 g of cis methyl 4-(N,N-dibenzylamino)-cyclohexyl-carboxylate (46% of theory), Melting point: 114°–116° C. $R_f$ value: 0.61 (silica gel; cyclohexane/ethyl acetate=4:1)

Yield: 25.5 g of trans methyl 4-(N,N-dibenzylamino)-cyclohexyl-carboxylate (22% of theory), Melting point: 71°–74° C. $R_f$ value: 0.56 (silica gel; cyclohexane/ethyl acetate=4:1)

The following compounds are obtained analogously:
(1) cis- and trans methyl 4-(N-benzyl-methylamino)-cyclohexyl-carboxylate The crude product is chromatographed with cyclohexane/ ethyl acetate in the ratio 20:1 over aluminium oxide of activity stage III.

cis methyl 4-(N-benzyl-methylamino)-cyclohexyl-carboxylate $R_f$ value: 0.35 (aluminium oxide; cyclohexane/ ethyl acetate=10:1)

trans methyl 4-(N-benzyl-methylamino)-cyclohexyl-carboxylate $R_f$ value: 0.27 (aluminium oxide; cyclohexane/ ethyl acetate=10:1)

EXAMPLE XXII

Trans methyl 4-aminocyclohexyl-carboxylate

A suspension of 25 g of trans methyl 4-(N,N-dibenzylamino)-cyclohexyl-carboxylate and 5.0 g of 10% palladium on charcoal in 500 ml of methanol is hydrogenated for one hour at 40° C. under a hydrogen pressure of 3.6 bar. The catalyst is filtered off and the filtrate is evaporated down.

Yield: 11.0 g oil (95% of theory), $R_f$ value: 0.69 (silica gel; methylene chloride/methanol/conc. ammonia solution= 4:1:0.25)

The following compounds are obtained analogously:
(1) cis methyl 4-aminocyclohexyl-carboxylate $R_f$ value: 0.69 (silica gel; methylene chloride/methanol/ conc. ammonia solution=4:1:0.25)
(2) trans methyl 4-(methylamino)-cyclohexyl-carboxylate $R_f$ value: 0.75 (silica gel; methylene chloride/methanol/ conc. ammonia solution=4:1:0.25)

EXAMPLE XXIII 6-(4-Cyanophenyl)-4-[[trans-4-(methoxycarbonyl)-cyclohexyl-aminocarbonyl]-2-[(morpholinocarbonyl)-methyl]-(2H)-pyridazin-3-one A suspension of 1.2 g of 4-carboxy-6-(4-cyanophenyl)-2-[(morpholinocarbonyl)methyl]-(2H)-pyridazin-3-one 1.29 g of 2-[(1H)-benzotriazol-1-yl]- 1,1,3,3-tetramethyl-uroniumtetrafluoroborate, 0.64 g of trans methyl- 4-aminocyclohexanecarboxylate-hydrochloride, 0.54 g of 1-hydroxy-(1H)-benzotriazole hydrate and 0.81 g of N-methylmorpholine in 100 ml of dimethylformamide is stirred for 16 hours at ambient temperature. The solvent is evaporated off under reduced pressure at a bath temperature of 80° C. and the remaining oil is chromatographed.

Yield: 1.38 g (83% of theory), Melting point: 195°–200° C. $R_f$ value: 0.63 (silica gel; methylene chloride/methanol=9:1)

Preparation of the End Compounds

EXAMPLE 1

6-(4-Amidinophenyl)-4-[(4-carboxybutyl)-aminocarbonyl]-2-methyl-(2H)-pyridazin- 3-one A solution of 300 mg of 6-[4-amidinophenyl)-4-[[4-(methoxycarbonyl)-butyl]-aminocarbonyl]-2-methyl-(2H)-pyridazin-3-one and 125 mg of lithium hydroxide-monohydrate in a mixture of 20 ml of tetrohydrofuran and 16 ml of water is stirred for 1½ hours at ambient temperature. Then 1.0 g of ammonium chloride is added and the mixture is stirred for 20 minutes. Excess tetrahydrofuran is suction filtered, washed with water and acetone and dried.

Yield: 250 mg 191% of theory), Melting point: over 250° C., Mass spectrum: 372 $(M+1)^+$ $R_f$ value: 0.24 (silica gel; methylene chloride/methanol/conc. ammonia solution=2:1:0.25)

The following compounds are obtained analogously:
(1) 6-(4-amidinophenyl)-4-[(3-carboxypropyl)-aminocarbonyl]-2-methyl-(2H)-pyridazin- 3-one 1N sodium hydroxide solution in methanol is used.

Melting point: from 280° C. (decomp.), Mass spectrum: 358 $(M+1)^+$ $R_f$ value: 0.26 (silica gel; methylene chloride/methanol/conc. ammonia solution=2:1:0.25)
(2) 6-(4-amidinophenyl)-4-[(2-carboxyethyl)-aminocarbonyl]-2-methyl-( 2H)-pyridazin-3-one Melting point: from 265° C. (decomp.), Mass spectrum: $(M+1)^+$ $R_f$ value: 0.19 (silica gel; methylene chloride/methanol/conc. ammonia solution=2:1:0.25)

| Calculated: | C 50.66 | H 5.58 | N 18.64 |
|---|---|---|---|
| Found: | 50.78 | 5.63 | 18.66 |

(3) 6-(4-amidinophenyl)-4-[(4-carboxybutyl)-aminocarbonyl]-2H-pyridazin- 3-one

Mass spectrum: 358 $(M+1)^+$ $R_f$ value: 0.27 (silica gel; methylene chloride/methanol/conc. ammonia solution=2:1:0.25)
(4) 6-(4-amidinophenyl)-4-[(trans-4-carboxycyclohexyl)-aminocarbonyl]- 2-methyl-(2H)-pyridazin-3-one Melting point: 263°–266° C., Mass spectrum: 398 $(M+1)^+$ $R_f$ value: 0.16 (silica gel; methylene chloride/methanol/conc. ammonia solution=2:1:0.25)

| Calc. × 1 H$_2$O: | C 57.82 | H 6.07 | N 16.86 |
|---|---|---|---|
| Found: | 57.99 | 6.08 | 16.92 |

(5) 6-(4-amidinophenyl)-4-[(cis-4-carboxycyclohexyl)-aminocarbonyl]-2-methyl-(2H)-pyridazin-3-one Melting point: 266°–269° C., Mass spectrum: 398 $(M+1)^+$ $R_f$ value: 0.15 (silica gel; methylene chloride/methanol/conc. ammonia solution=2:1:0.25)

(6) 6-(4-amidinophenyl)-4-[[4-(carboxymethyl)-phenyl]-aminocarbonyl]-2-methyl-(2H)-pyridazin-3-one 1N sodium hydroxide solution is used and the solvent is a mixture of methylene chloride/methanol/tetrahydrofuran in the ratio 1:1:0.6.

Melting point: from 255° C. (decomp.) Mass spectrum: 406 $(M+1)^+$
(7) 6-(4-amidinophenyl)-3-[4-(2-carboxyethyl)-phenylamino]-pyridazine Melting point: above 260° C., $R_f$ value: 0.09 (silica gel; methylene chloride/methanol/conc. ammonia solution=4:1:0.25)

| Calc. × 0.5 H$_2$O: | C 64.85 | H 5.44 | N 18.90 |
|---|---|---|---|
| Found: | 64.61 | 5.64 | 18.67 |

(8) 6-(4-amidinophenyl)-3-[4-(2-carboxyethyl)-phenyloxy]-pyridazine

The crude product is chromatographically purified.

Mass spectrum: 363 $(M+1)^+$ $R_f$ value: 0.12 (silica gel; methylene chloride/methanol/conc. ammonia solution=2:1:0.25)
(9) 6-(4-amidinophenyl)-3-[(3-carboxyphenyl)-methylamino]-pyridazine Melting point: over 260° C., Mass spectrum: 348 $(M+1)^+$ $R_f$ value: 0.22 (silica gel; methylene chloride/methanol/conc. ammonia solution=2:1:0.25)
(10) 6-(4-amidinophenyl)-3-[3-[(carboxymethyl)-oxy]-piperidino]-pyridazine Melting point: from 278° C., Mass spectrum: 356 $(M+1)^+$ $R_f$ value: 0.21 (silica gel; methylene chloride/methanol/conc. ammonia solution=2:1:0.25)
(11) 6-(4-amidinophenyl)-3-[(trans-4-carboxycyclohexyl)-amino]-pyridazine Mass spectrum: 340 $(M+1)^+$ $R_f$ value: 0.14 (silica gel; methylene chloride/methanol/conc. ammonia solution=2:1:0.25)
(12) 6-(4-amidinophenyl)-3-[N-(trans-4-carboxycyclohexyl) -N-methylamino]-pyridazine Melting point: 308°–310° C., Mass spectrum: 368 $(M+1)^+$ $R_f$ value: 0.25 (silica gel; methylene chloride/methanol/conc. ammonia solution=2:1:0.25)
(13) 2-(4-amidinophenyl)-5-[4-(carboxymethyl)-piperidinocarbonyl]-(3H)-pyrimidin-4-one Mass spectrum: 383 $M^+$ $R_f$ value: 0.09 (silica gel; methylene chloride/methanol/conc. ammonia solution=2:1:0.25)

| Calc. × H$_2$O: | 56.85 | 5.78 | N 17.45 |
|---|---|---|---|
| Found: | 57.06 | 5.59 | 17.15 |

(14) 2-(4-amidinophenyl)-5-[4-(carboxymethyl)-piperidinocarbonyl]-4-methoxy-pyrimidine Mass spectrum: 398 $(M+1)^+$ $R_f$ value: 0.38 (silica gel; methylene chloride/methanol/conc. ammonia solution=2:1:0.25)
(15) 2-(4-amidinophenyl)-5-[4-(carboxymethyl)-piperidinocarbonyl] -pyrimidine Mass spectrum: 368 $(M+1)^+$ $R_f$ value: 0.20 (silica gel; methylene chloride/methanol/conc. ammonia solution=2:1:0.25)
(16) 6-(4-amidinophenyl)-4-[N-(trans-4-carboxycyclohexyl)-N-methyl-aminocarbonyl]- 2-methyl-(2H)-pyridazin-3-one Mass spectrum: 412 $(M+1)^+$ $R_f$ value: 0.11 (silica gel; methylene chloride/methanol/conc. ammonia solution=4:1:0.25)

(17) 6-(4-amidinophenyl)-2-(carbamoyl-methyl)-4-[(trans-4-carboxycyclohexyl)-aminocarbonyl]-(2H)-pyridazin-3-one

(18) 6-(4-amidinophenyl)-2-benzyl-4-[(trans-4-carboxycyclohexyl)-aminocarbonyl]-(2H)-pyridazin-3-one Mass spectrum: 474 (M+H)$^+$ R$_f$ value: 0.14 (silica gel; methylene chloride/methanol/conc. ammonia solution= 4:1:0.25)

(19) 6-(4-amidinophenyl)-4-[(trans-4-carboxycyclohexyl)-aminocarbonyl]-(2H)-pyridazin-3-one

(20) 3-(4-amidinophenyl)-5-[(trans-4-carboxycyclohexyl)-aminocarbonyl]-pyridazine Melting point: 292°–296° C., Mass spectrum: 368 (M+1)$^+$ R$_f$ value: 0.07 (silica gel; methylene chloride/methanol/conc. ammonia solution=4:1:0.25)

(21) 6-(4-amidinophenyl)-4-[(trans-4-carboxycyclohexyl)-aminocarbonyl]- 3-methoxy-pyridazine Melting point: sintering from 270°–280° C., Mass spectrum: 398 (M+1)$^+$ R$_f$ value: 0.26 (silica gel; methylene chloride/methanol/conc. ammonia solution=2:1:0.25)

(22) 6-(4-amidinophenyl)-4-[(trans-4-carboxycyclohexyl)-aminocarbonyl]-3-morpholino-pyridazine Melting point: 265°–270° C., Mass spectrum: 453 (M+1)$^+$ R$_f$ value: 0.28 (silica gel; methylene chloride/methanol/conc. ammonia solution=2:1:0.25)

(23) 6-(4-amidinophenyl)-4-[(trans-4-carboxycyclohexyl)-aminocarbonyl]-3-ethoxy-pyridazine

(24) 6-(4-amidinophenyl)-4-[(trans-4-carboxycyclohexyl)-aminocarbonyl]-3-thiomorpholino-pyridazine

(25) 6-(4-amidinophenyl)-4-[(trans-4-carboxycyclohexyl)-aminocarbonyl]-3-dimethylamino-pyridazine

(26) 3-(4-acetyl-piperazino)-6-(4-amidinophenyl)-4-[(trans-4-carboxycyclohexyl)-aminocarbonyl]-pyridazine

(27) 6-(4-amidinophenyl)-4-[(trans-4-carboxycyclohexyl)-aminocarbonyl]- 3-piperidino-pyridazine

(28) 6-(4-amidinophenyl)-4-[(trans-4-carboxycyclohexyl)-aminocarbonyl]- 3-pyrrolidino-pyridazine

(29) 6-(4-amidinophenyl)-4-[(trans-4-carboxycyclohexyl)-aminocarbonyl]-2-[(N,N-dimethyl-aminocarbonyl)-methyl]-(2H)-pyridazin- 3-one

(30) 6-(4-amidinophenyl)-4-[(trans-4-carboxycyclohexyl)-aminocarbonyl]- 2-[(morpholinocarbonyl)-methyl]-(2H)-pyridazin-3-one-hydrochloride Instead of adding ammonium chloride the mixture is acidified with 1N hydrochloric acid.

Melting point: sintering from 245° C., Mass spectrum: 511 (M+H)$^+$ R$_f$ value: 0.16 (silica gel; methylene chloride/methanol/conc. ammonia solution=2:1:0.25)

(31) 6-(4-amidinophenyl)-4-[(trans-4-carboxycyclohexyl)-aminocarbonyl]-2-ethyl-(2H)-pyridazin-3-one

(32) 5-(4-amidinophenyl)-3-[(trans-4-carboxycyclohexyl)-aminocarbonyl]-pyridin-2-one

(33) 5-(4-amidinophenyl)-3-[(trans-4-carboxycyclohexyl)-aminocarbonyl]- 1-methyl-pyridin-2-one

(34) 5-(4-amidinophenyl)-3-[(trans-4-carboxycyclohexyl)-aminocarbonyl]-( 1H)-pyrazin-2-one

(35) 6-(4-amidinophenyl)-4-[(trans-4-carboxycyclohexyl)-aminocarbonyl]- 2-phenyl-(2H)-pyridazin-3-one

(36) 6-(4-amidino-2-methyl-phenyl)-4-[(trans-4-carboxycyclohexyl)-aminocarbonyl]- 2-methyl-(2H)-pyridazin-3-one

(37) 6-(4-amidino-2-fluoro-phenyl)-4-[(trans-4-carboxycyclohexyl)-aminocarbonyl]- 2-methyl-(2H)-pyridazin-3-one

(38) 3-(4-amidinophenyl)-5-[(trans-4-carboxycyclohexyl)-aminocarbonyl]-(1H)-1,2,4-triazin-6-one

(39) 6-(4-amidinophenyl)-4-[[[(carboxymethyl)-aminocarbonyl]-methyl]-aminocarbonyl]-2-methyl-(2H)-pyridazin-3-one

(40) 6-(4-amidinophenyl)-4-[[[N-(carboxymethyl)-N-methyl-aminocarbonyl]-methyl]-aminocarbonyl]-2-methyl-(2H)-pyridazin-3-one

(41) 4-[[2-[N-acetyl-N-(carboxymethyl)-amino]-ethyl]-aminocarbonyl]- 6-(4-amidinophenyl)-2-methyl-(2H)-pyridazin-3-one

(42) 6-(4-amidinophenyl)-4-[[2-[(carboxymethyl)-oxy]-ethyl]-aminocarbonyl]- 2-methyl-(2H)-pyridazin-3-one

(43) 6-(4-amidinophenyl)-4-[[2-[N-(carboxymethyl)-N-(methanesulphonyl)-amino]-ethyl]-aminocarbonyl]-2-methyl-(2H)-pyridazin- 3-one

(44) 6-(4-amidinophenyl)-4-[[2-[N-benzyl-N-(carboxymethyl)-amino]-ethyl]-aminocarbonyl]-2-methyl-(2H)-pyridazin-3-one

(45) 6-(4-amidinophenyl)-4-[(3-carboxy-prop-2-enyl)-aminocarbonyl]-2-methyl-(2H)-pyridazin-3-one

(46) 5-(4-amidinophenyl)-2-[4-(carboxymethyl)-piperidinocarbonyl]-pyrimidine

(47) 3-amidino-6-[4-4-(carboxymethyl)-piperidinocarbonyl]-phenyl]-pyridine

(48) 5-(4-amidinophenyl)-2-[(3-carboxypropyl )-aminocarbonyl]-pyrimidine

(49) 5-(4-amidinophenyl)-2-[N-(3-carboxypropyl)-N-methylaminocarbonyl]-pyrimidine

(50) 5-(4-amidinophenyl)-2-[(4-carboxybutyl)-aminocarbonyl]-pyrimidine

(51) 2-[[2-[N-acetyl-N-(carboxymethyl)-amino]-ethyl]-aminocarbonyl]- 5-(4-amidinophenyl)-pyrimidine

(52) 5-(4-amidinophenyl)-2-[4-(carboxymethyl)-piperidinocarbonyl]-pyrazine

(53) 2-(4-amidinophenyl)-5-[4-(carboxymethyl)-piperidinocarbonyl]- 3-methyl-(3H)-pyrimidin-4-one

(54) 3-amidino-6-[4-[(trans-4-carboxycyclohexyl)-aminocarbonyl]-phenyl]-pyridine

(55) 5-(4-amidino-3-fluorophenyl)-2-[4-(carboxymethyl)-piperidinocarbonyl]-pyrimidine

(56) 5-(4-amidino-2-chlorophenyl)-2-[4-(carboxymethyl)-piperidinocarbonyl]-pyrimidine

(57) 2-(4-amidino-2-methyl-phenyl)-5-[4-(carboxymethyl)-piperidinocarbonyl]-pyrimidine

(58) 5-(5-amidinopyridin-2-yl)-2-[4-(carboxymethyl)-piperidinocarbonyl]-pyrimidine

(59) 5-(4-amidinophenyl)-2-[4-(carboxymethyl)-piperidinocarbonyl]-pyridine

(60) 5-amidino-2-[4-4-(carboxymethyl)-piperidinocarbonyl]-phenyl]-pyrimidine

(61) 5-(4-amidinophenyl)-2-[4-(carboxymethyl)-piperazinocarbonyl]-pyrimidine

(62) 5-(4-amidinophenyl)-2-[4-(2-carboxyethyl)-piperazinocarbonyl]-pyrimidine

(63) 5-(4-amidinophenyl)-2-[4-(1-carboxyethyl)-piperidinocarbonyl]-pyrimidine

(64) 5-(4-amidinophenyl)-2-[4-(carboxymethyl)-3-oxy-piperazinocarbonyl]-pyrimidine

(65) 5-(4-amidinophenyl)-2-[3-(carboxymethyl)-piperidinocarbonyl]-pyrimidine

(66) 6-(4-amidinophenyl)-3-[3-[(carboxymethyl)-oxy]-pyrrolidino]-pyridazine

(67) 6-(4-amidinophenyl)-3-[3-(2-carboxyethyl)-piperidino]-pyridazine

(68) 6-(4-amidinophenyl)-3-[4-(2-carboxyethyl)-piperidino]-pyridazine

(69) 6-(4-amidinophenyl)-3-[4-(2-carboxyethyl)-piperazino]-pyridazine

(70) 6-(4-amidinophenyl)-3-[4-(carboxymethyl)-piperidino]-pyridazine

(71) 6-(4-amidinophenyl)-3-[4-(carboxymethyl)-piperazino]-pyridazine

(72) 6-(4-amidinophenyl)-3-[[4-(carboxymethyl)-cyclohexylamino]-pyridazine
(73) 6-(4-amidinophenyl)-3-[N-[4-(carboxymethyl)-cyclohexyl]-N-methyl-amino]-pyridazine
(74) 6-(4-amidinophenyl)-3-[N-(4-carboxybutyl)-N-methyl-amino]-pyridazine
(75) 6-(4-amidinophenyl)-3-[N-(5-carboxypentyl)-N-methylamino]-pyridazine
(76) 3-amidino-6-[4-[(4-carboxybutyl)-oxy]-phenyl]-pyridine
(77) 2-amidino-5-[4-[(5-carboxypentyl)-oxy]-phenyl]-pyrazine
(78) 5-(4-amidinophenyl)-2-[trans-4-(carboxycyclohexyl)-amino]-pyrimidine
(79) 5-(4-amidinophenyl)-2-[trans-4-(carboxycyclohexyl)-amino]-pyridine
(80) 5-amidino-2-[4-[[(2-carboxyethyl)-aminocarbonyl]-methyloxy]-phenyl]-pyrimidine
(81) 5-amidino-2-[4-[(4-carboxy-piperidinocarbonyl)-methyloxy]-phenyl]-1,3-thiazole
(82) 2-amidino-5-[4-[[(carboxymethyl)-aminocarbonyl]-methyloxy]phenyl]-pyrimidine
(83) 6-(4-amidinophenyl)-3-amino-4-[N-(trans- 4-carboxycyclohexyl)-N-methyl-aminocarbonyl]-pyridazine
(84) 6-(4-amidinophenyl)-4-[(trans-4-carboxycyclohexyl)-aminocarbonyl]- 2-[[(1-carboxy-2-phenyl-ethyl)-aminocarbonyl]-methyl]-( 2H)-pyridazin-3-one
(85) 6-(4-amidinophenyl)-4-[N-(trans-4-carboxycyclohexyl)-aminocarbonyl]-N-methyl-aminocarbonyl]- 2-[[(1-carboxyethyl)-aminocarbonyl]-methyl]-( 2H )-pyridazin-3-one
(86) 2-[4-[N-[(3-carboxyprop-1-yl)-carbonyl]-N-methylamino]-phenyl]- 5-(N-methyl-amidino)-pyridine
(87) 5-(4-amidinophenyl)-2-[[4-(carboxymethyl)-piperidino]-methyl]-pyrimidine
(88) 5-amidino-2-[4-[(4-carboxybutyl)-aminosulphonyl]-phenyl]-pyrimidine
(89) 5-(4-amidinophenyl)-2-[(4-(carboxymethylidene)-piperidinocarbonyl]-pyrimidine
(90) 2-(4-amidinophenyl)-5-[4,4-bis-(carboxymethyl)-piperidinocarbonyl]-pyrimidine
(91) 1-(4-amidinophenyl)-5-[(trans-4-carboxycyclohexyl)-aminocarbonyl]-( 1H)-pyridin-2-one
(92) 4-[4-[N-(n-butyl)-amidino]-phenyl]-1-[[(2-carboxyethyl)-aminocarbonyl]-methyl]-(1H)-pyridin-2-one
(93) 2-[4-(aminomethyl)-phenyl]-5-[4-(carboxymethyl)-piperidinocarbonyl]-( 3H)-pyrimidin-4-one-hydrochloride Instead of adding ammonium chloride the mixture is acidified with 1N hydrochloric acid.

Mass spectrum: 371 (M+H)⁺ R$_f$ value: 0.01 (silica gel; methylene chloride/methanol/conc. ammonia solution= 2:1:0.25)

(94) 6-(4-amidinophenyl)-4-[4-(carboxymethyl)-piperidinocarbonyl]- 2-[(morpholinocarbonyl)-methyl]-(2H)-pyridazin- 3-one
(95) 6-(4-amidinophenyl)-4-[N-(trans -4-carboxy-cyclohexyl)-N-methyl-aminocarbonyl]- 2-[(morpholinocarbonyl)-methyl]-(2H )-pyridazin- 3-one
(96) 2-(4-amidinophenyl)-5-[(trans-4-carboxycyclohexyl)-aminocarbonyl]- 4-methoxy-pyrimidine
(97) 2-(4-amidinophenyl)-5-1N-(trans-4-carboxycyclohexyl)-N-methyl-aminocarbonyl]-pyrimidine
(98) 2-(4-amidinophenyl)-5-[N-(trans-4-carboxycyclohexyl)-N-methyl-aminocarbonyl]-4-ethoxy-pyrimidine

EXAMPLE 2

6-(4-Amidinophenyl)-4-[[trans-4-(methoxycarbonyl)-cyclohexyl]-aminocarbonyl]-2-methyl-(2H)-pyridazin-3-one 2.40 g of 6-(4-cyanophenyl)-4-[[trans-4-(methoxycarbonyl)-cyclohexyl]-aminocarbonyl]-2-methyl-(2H)-pyridazin-3-one are dissolved in 50 ml of absolute methylene chloride and 500 ml of absolute methanol. Whilst cooling in a bath of ice/water, dry HCl gas is passed through for 2 hours (washing bottle containing concentrated sulphuric acid provided in front). The reaction solution is stirred at ambient temperature and the conversion is monitored by thin layer chromatography. After reaction is complete the reaction solution is evaporated down in vacuo at a bath temperature of 25°–35° C., the residue is dissolved in 300 ml of absolute methanol and 15.0 g of ammonium carbonate are added to the solution which is stirred thoroughly. It is stirred for 16 hours at ambient temperature, the precipitate is suction filtered and washed with methanol and water.

Yield: 1.2 g (48% of theory), Melting point: 198°–205° C.
Mass spectrum: 412 (M+1)⁺

By evaporating down the filtrate, triturating the residue with water and suction filtering, a further 0.75 g of product are obtained.

Melting point: 198°–205° C. R$_f$ value: 0.33 (silica gel; methylene chloride/methanol/conc. ammonia solution= 4:1:0.25)

| | | | |
|---|---|---|---|
| Calculated: | C 61.30 | C 6.12 | N 17.02 |
| Found: | 61.05 | 6.31 | 16.91 |

The following compounds are obtained analogously:
(1) 6-(4-amidinophenyl)-4-[[4-(methoxycarbonyl)-butyl]-aminocarbonyl]- 2-methyl-(2H)-pyridazin-3-one The starting material used is 6-(4-cyanophenyl)-4-[(4-carboxybutyl)-aminocarbonyl]- 2-methyl-(2H)-pyridazin-3-one Mass spectrum: 386 (M+1)⁺ R$_f$ value: 0.70 (silica gel; methylene chloride/methanol/conc. ammonia solution= 2:1:0.25)

(2) 6-(4-amidinophenyl)-4-[[3-(methoxycarbonyl)-propyl]-aminocarbonyl]- 2-methyl-(2H)-pyridazin-3-one R$_f$ value: 0.31 (silica gel; methylene chloride/methanol/ conc. ammonia solution=2:1:0.25)

(3) 6-(4-amidinophenyl)-4-[[2-(methoxycarbonyl)-ethyl]-aminocarbonyl]-2-methyl-(2H)-pyridazin-3-one The starting material used is 6-(4-cyanophenyl)-4-[[2-ethoxycarbonyl)-ethyl]-aminocarbonyl]-2-methyl-(2H)-pyridazin-3-one Melting point: 182°–185° C., Mass spectrum: 358 (M+1)⁺ R$_f$ value: 0.27 (silica gel; methylene chloride/methanol/ conc. ammonia solution=4:1:0.25)

(4) 6-(4-amidinophenyl)-4-[[4-(methoxycarbonyl)-butyl]-aminocarbonyl]-(2H)-pyridazin-3-one The starting material used is 6-(4-cyanophenyl)-4-[(4-carboxybutyl)-aminocarbonyl]-(2H)-pyridazin-3-one. The crude product is purified by chromatography.

Mass spectrum: 372 (M+1)⁺ R$_f$ value: 0.40 (silica gel; methylene chloride/methanol/conc. ammonia solution= 4:1:0.25)

(5) 6-(4-amidinophenyl)-4-[[cis-4-(methoxycarbonyl)-cyclohexyl]-aminocarbonyl]- 2-methyl-(2H)-pyridazin-3-one Mass spectrum: 412 (M+1)⁺ R_f value: 0.24 (silica gel; methylene chloride/methanol/conc. ammonia solution= 4:1:0.25)

(6) 6-(4-amidinophenyl)-4-[[4-[(methoxycarbonyl)-methyl]-phenyl]-aminocarbonyl]-2-methyl-(2H)-pyridazin-3-one-hydrochloride Melting point: from 265° C. (decomp.), Mass spectrum: 402 (M+1)⁺ R_f value: 0.34 (silica gel; methylene chloride/methanol/conc. ammonia solution=4:1:0.25)

(7) 6-(4-amidinophenyl)-3-[4-[2-(methoxycarbonyl)-ethyl]-phenylamino]-pyridazine-hydrochloride The crude product is purified by chromatography.

Melting point: over 200° C., Mass spectrum: 376 (M+1)⁺ R_f value: 0.15 (silica gel; methylene chloride/methanol/conc. ammonia solution=4:1:0.25)

| Calc.: × 1 HCl × 1 H₂O: | C 58.67 | H 5.63 | N 16.29 | Cl 8.25 |
|---|---|---|---|---|
| Found: | 58.82 | 5.74 | 16.45 | 8.04 |

(8) 6-(4-amidinophenyl)-3-[4-[2-(methoxycarbonyl)-ethyl]-phenyloxy]-pyridazine

The crude product is purified by chromatography.

Melting point: 178°–181° C., Mass spectrum: 377 (M+1)⁺ R_f value: 0.40 (silica gel; methylene chloride/methanol/conc. ammonia solution=4:1:0.25)

| Calculated: | C 67.01 | H 5.36 | N 14.88 |
|---|---|---|---|
| Found: | 66.72 | 5.31 | 14.61 |

(9) 6-(4-amidinophenyl)-3-[4-[(methoxycarbonyl)-methyloxy]-phenyloxy]-pyridazine and 6-(4-amidinophenyl)-3-[4-(carboxymethyloxy)-phenyloxy]-pyridazine The crude product is chromatographed. A mixture of the methylester and the free acid is obtained. By triturating the mixture with methylene chloride/methanol (1:1) and suction filtering the precipitate the free acid can be concentrated.

R_f value (methylester): 0.58 (silica gel; methylene chloride/methanol/conc. ammonia solution=2:1:0.25)

R_f value (acid): 0.44 (silica gel; methylene chloride/methanol/conc. ammonia solution 2:1:0.25)

Mass spectrum (acid): 365 (M+1)⁺

(10) 6-(4-amidinophenyl)-3-[[3-(methoxycarbonyl)-phenyl]-methylamino]-pyridazine-hydrochloride The reaction is carried out in methanol. The crude product is purified by chromatography.

Mass spectrum: 362 (M+1)⁺ R_f value: 0.34 (silica gel; methylene chloride/methanol/conc. ammonia solution= 4:1:0.25)

(11) 6-(4-amidinophenyl)-3-[3-[(methoxycarbonyl)-methyloxy]-piperidino]-pyridazine-hydrochloride The starting product used is 6-(4-cyanophenyl)-3-[3-[(ethoxycarbonyl)-methyloxy]-piperidino]-pyridazine. The reaction is carried out in methanol.

R_f value: 0.23 (silica gel; methylene chloride/methanol/conc. ammonia solution=4:1:0.25)

(12) 6-(4-amidinophenyl)-3-[[trans-4-(methoxycarbonyl)-cyclohexyl]-amino]-pyridazine The reaction is carried out in methanol. The crude product is purified by chromatography.

Mass spectrum: 354 (M+1)⁺ R_f value: 0.28 (silica gel; methylene chloride/methanol/conc. ammonia solution= 4:1:0.25)

(13) 6-(4-amidinophenyl)-3-[N-[trans-4-(methoxycarbonyl)-cyclohexyl]-N-methyl-amino]-pyridazine-hydrochloride The reaction is carried out in methanol. The crude product is purified by chromatography.

Melting point: sintering from 155° C., Mass spectrum: 368 (M+1)⁺ R_f value: 0.21 (silica gel; methylene chloride/methanol/conc. ammonia solution=4:1:0.25)

(14) 2-(4-amidinophenyl)-5-[4-[(methoxycarbonyl)-methyl]-piperidinocarbonyl]-( 3H)-pyrimidin-4-one-hydrochloride The reaction is carried out in methanol. The crude product is purified by chromatography.

Mass spectrum: 398 (M+1)⁺ R_f value: 0.13 (silica gel; methylene chloride/methanol/conc. ammonia solution= 4:1:0.25)

(15) 2-(4-amidinophenyl)-4-methoxy-5-[4-[(methoxycarbonyl)-methyl]-piperidinocarbonyl]-pyrimidine-hydrochloride The starting material used is 4-chloro-2-(4-cyanophenyl)-5-[4-[(methoxycarbonyl)-methyl]-piperidinocarbonyl]-pyrimidine. The reaction is carried out in methanol. The crude product is purified by chromatography.

Mass spectrum: 412 (M+H)⁺ R_f value: 0.07 (silica gel; methylene chloride/methanol=6:1)

(16) 2-(4-amidinophenyl)-5-[4-[(methoxycarbonyl)-methyl]-piperidinocarbonyl]-pyrimidine-hydrochloride The reaction is carried out in methanol. The crude product is purified by chromatography.

Mass spectrum: 382 (M+H)⁺ R_f value: 0.29 (silica gel; methylene chloride/methanol=4:1)

(17) 6-(4-amidinophenyl)-4-[N-[trans-4-(methoxycarbonyl)-cyclohexyl]-N-methyl-aminocarbonyl]-2-methyl-(2H)-pyridazin-3-one-hydrochloride Melting point: sintering 200°–215° C., Mass spectrum: 426 (M+H)⁺ R_f value: 0.52 (silica gel; methylene chloride/methanol/conc. ammonia solution=4:1:0.25)

(18) 6-(4-amidinophenyl)-2-(carbamoyl-methyl)-4-[[trans-4-(methoxycarbonyl)-cyclohexyl]-aminocarbonyl]-(2H)-pyridazin-3-one-hydrochloride

(19) 6-(4-amidinophenyl)-2-benzyl-4-[[trans-4-(methoxycarbonyl)-cyclohexyl]-aminocarbonyl]-(2H)-pyridazin-3-one The reaction is carried out in methanol. The crude product is purified by chromatography.

Melting point: 168°–173° C., Mass spectrum: 488 (M+H)⁺ R_f value: 0.27 (silica gel; methylene chloride/methanol/conc. ammonia solution=4:1:0.25)

(20) 6-(4-amidinophenyl)-4-[[trans-4-(methoxycarbonyl)-cyclohexyl]-aminocarbonyl]-(2H)-pyridazin-3-one-hydrochloride

(21) 3-(4-amidinophenyl)-5-[[trans-4-(methoxycarbonyl)-cyclohexyl]-aminocarbonyl]-pyridazine -hydrochloride Melting point: 275°–280° C., Mass spectrum: 382 (M+1)⁺ R_f value: 0.18 (silica gel; methylene chloride/methanol/conc. ammonia solution=4:1:0.25)

(22) 6-(4-amidinophenyl)-3-methoxy-4-[[trans-4-(methoxycarbonyl)-cyclohexyl]-aminocarbonyl]-pyridazine-hydrochloride Mass spectrum: 412 (M+1)⁺ R_f value: 0.29 (silica gel; methylene chloride/methanol/conc. ammonia solution= 4:1:0.25)

(23) 6-(4-amidinophenyl)-4-[[trans-4-(methoxycarbonyl)-cyclohexyl]-aminocarbonyl]-3-morpholino-pyridazine-hydrochloride Melting point: from 290° C. (decomp.), Mass spectrum: 467 (M+1)⁺ R_f value: 0.16 (silica gel; methylene chloride/methanol/conc. ammonia solution=4:1:0.25)

(24) 6-(4-amidinophenyl)-2-ethoxy-4-[[trans-4-(ethoxycarbonyl)-cyclohexyl]-aminocarbonyl]-pyridazine-hydrochloride The reaction is carried out in absolute ethanol.

(25) 6-(4-amidinophenyl)-4-[[trans-4-(methoxycarbonyl)-cyclohexyl]-aminocarbonyl]-3-thiomorpholino-pyridazine-hydrochloride
(26) 6-(4-amidinophenyl)-3-dimethylamino-4-[[trans-4-(methoxycarbonyl)-cyclohexyl]-aminocarbonyl]-pyridazine-hydrochloride
(27) 3-(4-acetyl-piperazino)-6-(4-amidinophenyl)-4-[[trans-4-(methoxycarbonyl)-cyclohexyl]-aminocarbonyl]-pyridazine-hydrochloride
(28) 6-(4-amidinophenyl)-4-[[trans-4-(methoxycarbonyl)-cyclohexyl]-aminocarbonyl]-3-piperidino-pyridazine-hydrochloride
(29) 6-(4-amidinophenyl)-4-[[trans-4-(methoxycarbonyl)-cyclohexyl]-aminocarbonyl]-3-pyrrolidino-pyridazine-hydrochloride
(30) 6-(4-amidinophenyl)-4-[[trans-4-(methoxycarbonyl)-cyclohexyl]-aminocarbonyl]-2-[(N,N-dimethyl-aminocarbonyl)-methyl]-( 2H)-pyridazin-3-one-hydrochloride
(31) 6-(4-amidinophenyl)-4-[[trans-4-(methoxycarbonyl)-cyclohexyl]-aminocarbonyl]-2-[(morpholinocarbonyl)-methyl]-(2H)-pyridazin- 3-one The reaction is carried out in methanol. The crude product is purified by chromatography.

Mass spectrum: 524 M$^+$ R$_f$ value: 0.22 (silica gel; methylene chloride/methanol/conc. ammonia solution=2:1:0.25)

(32) 6-(4-amidinophenyl)-2-ethyl-4-[[trans-4-(methoxycarbonyl)-cyclohexyl]-aminocarbonyl]-(2H)-pyridazin-3-one-hydrochloride
(33) 5-(4-amidinophenyl)-3-[[trans-4-(methoxycarbonyl)-cyclohexyl]-aminocarbonyl]-(1H)-pyridin-2-one-hydrochloride
(34) 5-(4-amidinophenyl)-3-[[trans-4-(methoxycarbonyl)-cyclohexyl]-aminocarbonyl]-1-methyl-(1H)-pyridin-2-one-hydrochloride
(35) 5-(4-amidinophenyl)-3-[[trans-4-(methoxycarbonyl)-cyclohexyl]-aminocarbonyl]-(1H)-pyrazin-2-one-hydrochloride
(36) 6-(4-amidinophenyl)-4-[[trans-4-(methoxycarbonyl)-cyclohexyl]-aminocarbonyl]-2-phenyl-(2H)-pyridazin-3-one-hydrochloride
(37) 6-(4-amidino-2-methyl-phenyl)-4-[[trans-4-(methoxycarbonyl)-cyclohexyl]-aminocarbonyl]-2-methyl-(2H)-pyridazin-3-one-hydrochloride
(38) 6-(4-amidino-2-fluoro-phenyl)-4-[[trans-4-(methoxycarbonyl)-cyclohexyl]-aminocarbonyl]-2-methyl-(2H)-pyridazin-3-one-hydrochloride
(39) 3-(4-amidino-5-[[trans-4-(methoxycarbonyl)-cyclohexyl]-aminocarbonyl]-(1H)-1,2,4-triazin-6-one-hydrochloride
(40) 6-(4-amidinophenyl)-4-[[[[(methoxycarbonyl)-methyl]-aminocarbonyl]-methyl]-aminocarbonyl]-2-methyl-(2H)-pyridazin-3-one-hydrochloride
(41) 6-(4-amidinophenyl)-4-[[[N-[(methoxycarbonyl)-methyl]-N-methyl-aminocarbonyl]-methyl]-aminocarbonyl]-2-methyl-(2H)-pyridazin- 3-one-hydrochloride
(42) 4-[[[N-acetyl-N-[(methoxycarbonyl)-methyl]-aminocarbonyl]-methyl]-aminocarbonyl]-6-(4-amidinophenyl)-2-methyl-(2H)-pyridazin- 2-one-hydrochloride
(43) 6-(4-amidinophenyl)-4-[[2-[[(methoxycarbonyl)-methyl]-oxy]-ethyl]-aminocarbonyl]-2-methyl-(2H)-pyridazin-3-one-hydrochloride
(44) 6-(4-amidinophenyl)-4-[[2-[N-(methanesulphonyl)-N-[(methoxycarbonyl)-methyl]-amino]-ethyl]-aminocarbonyl]-2-methyl-(2H)-pyridazin-3-one-hydrochloride
(45) 6-(4-amidinophenyl)-4-[[2-[N-benzoyl-N-[(methoxycarbonyl)-methyl]-amino]-ethyl]-aminocarbonyl]-2-methyl-(2H)-pyridazin-3-one-hydrochloride
(46) 6-(4-amidinophenyl)-2-methyl-4-[[3-(tetrazol-5-yl)-propyl]-aminocarbonyl]-(2H)-pyridazin-3-one-hydrochloride
(47) 6-(4-amidinophenyl)-2-methyl-4-[[4-(tetrazol-5-yl)-butyl]-aminocarbonyl]-(2H)-pyridazin-3-one-hydrochloride
(48) 6-(4-amidinophenyl)-2-methyl-4-[(3-phosphono-propyl)-aminocarbonyl]-(2H)-pyridazin-3-one-hydrochloride
(49) 6-(4-amidinophenyl)-2-methyl-4-[[4-(O-methyl-phosphono)-butyl]-aminocarbonyl]-(2H)-pyridazin-3-one-hydrochloride
(50) 6-(4-amidinophenyl)-2-methyl-4-[(4-sulphobutyl)-aminocarbonyl]-(2H)-pyridazin-3-one-hydrochloride
(51) 5-(4-amidinophenyl)-2-[4-[(methoxycarbonyl)-methyl]-piperidinocarbonyl]-pyrimidine-hydrochloride
(52) 3-amidino-6-[4-4-[(methoxycarbonyl)-methyl]-piperidinocarbonyl]-phenyl]-pyridine-hydrochloride
(53) 5-(4-amidinophenyl)-2-[[3-(methoxycarbonyl)-propyl]-aminocarbonyl]-pyrimidine-hydrochloride
(54) 5-(4-amidinophenyl)-2-[N-[3-(methoxycarbonyl)-propyl]-N-methyl-aminocarbonyl]-pyrimidine-hydrochloride
(55) 5-(4-amidinophenyl)-2-[[4-(methoxycarbonyl)-butyl]-aminocarbonyl]-pyrimidine-hydrochloride
(56) 2-[[2-[N-acetyl-N-[(methoxycarbonyl)-methyl]-amino]-ethyl]-aminocarbonyl]-5-(4-amidinophenyl)-pyrimidine-hydrochloride
(57) 5-(4-amidinophenyl)-2-[4-[(methoxycarbonyl)-methyl]-piperidinocarbonyl]-pyrazine-hydrochloride
(58) 2-(4-amidinophenyl)-5-[4-[(methoxycarbonyl)-methyl]-piperidinocarbonyl]-3-methyl-(3H)-pyrimidin-4-one-hydrochloride
(59) 3-amidino-6-[4-[[trans-4-(methoxycarbonyl)-cyclohexyl]-aminocarbonyl]-phenyl]-pyridine-hydrochloride
(60) 5-(4-amidino-3-fluorophenyl)-2-[4-[(methoxycarbonyl)-methyl]-piperidinocarbonyl]-pyrimidine-hydrochloride
(61) 5-(4-amidino-2-chlorophenyl)-2-[4-[(methoxycarbonyl)-methyl]-piperidinocarbonyl]-pyrimidine-hydrochloride
(62) 5-(4-amidino-2-methyl-phenyl)-2-[4-[(methoxycarbonyl)-methyl]-piperidinocarbonyl]-pyrimidine-hydrochloride
(63) 5-(5-amidinopyridin-2-yl )-2-[4-[(methoxycarbonyl)-methyl]-piperidinocarbonyl]-pyrimidine-hydrochloride
(64) 5-(4-amidinophenyl)-2-[4-[(methoxycarbonyl)-methyl]-piperidinocarbonyl]-pyridine-hydrochloride
(65) 5-amidino-2-[4-[4-[(methoxycarbonyl)-methyl]-piperidinocarbonyl]-phenyl]-pyrimidine-hydrochloride
(66) 5-(4-amidinophenyl)-2-[4-[(methoxycarbonyl)-methyl]-piperazinocarbonyl]-pyrimidine-hydrochloride
(67) 5-(4-amidinophenyl)-2-[4-[2-(methoxycarbonyl)-ethyl]-piperazinocarbonyl]-pyrimidine-hydrochloride
(68) 5-(4-amidinophenyl)-2-[4-[1-(methoxycarbonyl)-ethyl]-piperidinocarbonyl]-pyrimidine-hydrochloride
(69) 5-(4-amidinophenyl)-2-[4-[(methoxycarbonyl)-methyl]-3-oxy-piperazinocarbonyl]-pyrimidine-hydrochloride
(70) 5-(4-amidinophenyl)-2-[3-[(methoxycarbonyl)-methyl]-piperidinocarbonyl]-pyrimidine-hydrochloride
(71) 6-(4-amidinophenyl)-3-[3-[[(methoxycarbonyl)-methyl]-oxy]-pyrrolidino]-pyridazine-hydrochloride
(72) 6-(4-amidinophenyl)-3-[3-[2-(methoxycarbonyl)-ethyl]-piperidino]-pyridazine-hydrochloride
(73) 6-(4-amidinophenyl)-3-[4-[2-(methoxycarbonyl)-ethyl]-piperidino]-pyridazine-hydrochloride
(74) 6-(4-amidinophenyl)-3-[4-[2-(methoxycarbonyl)-ethyl]-piperazino]-pyridazine-hydrochloride

(75) 6-(4-amidinophenyl)-3-[4-[(methoxycarbonyl)-methyl]-piperidino]-pyridazine-hydrochloride
(76) 6-(4-amidinophenyl)-3-[4-[(methoxycarbonyl)-methyl]-piperazino]-pyridazine-hydrochloride
(77) 6-(4-amidinophenyl)-3-[[4-[(methoxycarbonyl)-methyl]-cyclohexyl]-amino]-pyridazine-hydrochloride
(78) 6-(4-amidinophenyl)-3-[N-[4-[(methoxycarbonyl)-methyl]-cyclohexyl]-N-methyl-amino]-pyridazine-hydrochloride
(79) 6-(4-amidinophenyl)-3-[N-[4-[(methoxycarbonyl)-butyl]-N-methyl-amino]-pyridazine-hydrochloride
(80) 6-(4-amidinophenyl)-3-[N-[5-(methoxycarbonyl)-pentyl]-N-methyl-amino]-pyridazine-hydrochloride
(81) 3-amidino-5-[4-[[4-(methoxycarbonyl)-butyl]-oxy]-phenyl]-pyridine-hydrochloride
(82) 2-amidino-5-[4-[[5-(methoxycarbonyl)-pentyl]-oxy]-phenyl]-pyrazine-hydrochloride
(83) 5-(4-amidinophenyl)-2-[[trans-4-(methoxycarbonyl)-cyclohexyl]-amino]-pyrimidine-hydrochloride
(84) 5-(4-amidinophenyl)-2-[[trans-4-(methoxycarbonyl)-cyclohexyl]-amino]-pyridine-hydrochloride
(85) 5-amidino-2-[4-[[[2-(methoxycarbonyl)-ethyl]-aminocarbonyl]-methyloxy]-phenyl]-pyrimidine-hydrochloride
(86) 5-amidino-2-[4-[[4-(methoxycarbonyl)-piperidinocarbonyl]-methyloxy]-phenyl]-1,3-thiazole-hydrochloride
(87) 2-amidino-5-[4-[[[(methoxycarbonyl)-methyl]-aminocarbonyl]-methyloxy]-phenyl]-pyrimidine-hydrochloride
(88) 6-(4-amidinophenyl)-4-[[3-(methoxycarbonyl)-prop-2-en-yl]-aminocarbonyl]-2-methyl-(2H)-pyridazin-3-one-hydrochloride
(89) 6-(4-amidinophenyl)-3-amino-4-[N-[trans-4-(methoxycarbonyl)-cyclohexyl]-N-methyl-aminocarbonyl]-pyridazine-hydrochloride
(90) 6-(4-amidinophenyl)-4-[[trans-4-(methoxycarbonyl)-cyclohexyl]-aminocarbonyl]-2-[[[1-(methoxycarbonyl)-2-phenylethyl]-aminocarbonyl]-methyl]-(2H)-pyridazin-3-one-hydrochloride
(91) 6-(4-amidinophenyl)-4-[N-[trans-4-(methoxycarbonyl)-cyclohexyl]-N-methyl-aminocarbonyl]-2-[[[1-(methoxycarbonyl)ethyl]-aminocarbonyl]-methyl]-(2H)-pyridazin-3-one-hydrochloride
(92) 2-[4-[N-[[3-(methoxycarbonyl)-propyl]-carbonyl]-N-methylamino]-phenyl]-5-(N-methyl-amidino)-pyridine-hydrochloride The imino ester is dissolved in absolute methanol and reacted with a 20-fold excess of a methanolic methylamine solution.

(93) 5-(4-amidinophenyl)-2-[[4-[(methoxycarbonyl)-methyl]-piperidino]-methyl]-pyrimidine-hydrochloride
(94) 5-amidino-2-[4-[[4-(methoxycarbonyl)-butyl]-amino-sulphonyl]-phenyl]-pyrimidine-hydrochloride
(95) 5-(4-amidinophenyl)-2-[4-[(methoxycarbonyl)-methylidene]-piperidinocarbonyl]-pyrimidine-hydrochloride
(96) 2-(4-amidinophenyl)-5-[4,4-bis-[(methoxycarbonyl)-methyl]-piperidinocarbonyl]-pyrimidine-hydrochloride
(97) 1-(4-amidinophenyl)-5-[[trans-4-(methoxycarbonyl)-cyclohexyl]-aminocarbonyl]-(1H)-pyridin-2-one-hydrochloride
(98) 4-[4-[N-(n-butyl)-amidino]-phenyl]-1-[[[2-(methoxycarbonyl)ethyl]-aminocarbonyl]-methyl]-(1H)-pyridin-2-one-hydrochloride The imino ester is taken up in absolute methanol and reacted with a 20-fold excess of a methanolic n-butylamine solution.

(99) 6-(4-amidinophenyl)-4-[4-[(methoxycarbonyl)-methyl]-piperidinocarbonyl]-2-[(morpholinocarbonyl)-methyl]-(2H)-pyridazin-3-one
(100) 6-(4-amidinophenyl)-4-[N-[trans-4-(methoxycarbonyl)-cyclohexyl]-N-methyl-aminocarbonyl]-2-[(morpholinocarbonyl)methyl]-(2H)-pyridazin-3-one
(101) 2-(4-amidinophenyl)-4-methoxy-5-[[trans-4-(methoxycarbonyl)-cyclohexyl]-aminocarbonyl]-pyrimidine
(102) 2-(4-amidinophenyl)-5-[N-[trans-4-(methoxycarbonyl)-cyclohexyl]-N-methyl-aminocarbonyl]-pyrimidine
(103) 2-(4-amidinophenyl)-4-ethoxy-5-[N-[trans-4-(ethoxycarbonyl)-cyclohexyl]-N-methyl-aminocarbonyl]-pyrimidine The starting material used is 4-chloro-2-(4-cyanophenyl)-5-[N-[trans-4-(methoxycarbonyl)-cyclohexyl]-N-methyl-aminocarbonyl]-pyrimidine. The reaction is carried out in ethanol.

EXAMPLE 3

6-[4-[N-(Methoxycarbonyl)-amidino]-phenyl]-4-[[trans-4-(methoxycarbonyl)-cyclohexyl]-aminocarbonyl]-2-methyl-(2H)-pyridazin- 3-one To a solution of 300 mg of 6-(4-amidinophenyl)-4-[[trans-4-(methoxycarbonyl)-cyclohexyl]-aminocarbonyl]-2-methyl-(2H)-pyridazin- 3-one in a mixture of 10 ml of methylene chloride and 10 ml of methanol are added 95 mg of methyl chloroformate. By the dropwise addition of 1N sodium hydroxide solution the pH of the solution is maintained at between 8.5 and 9.0. The reaction is monitored by thin layer chromatography. After 1½ hours another 0.1 ml of methyl chloroformate are added. After 3 hours the organic solvent is evaporated off, the aqueous phase remaining is diluted with water and extracted three times with methylene chloride. After the organic phase has been dried over sodium sulphate the solvent is evaporated off and the solids remaining are chromatographed over silica gel.

Yield: 290 mg (85% of theory), Mass spectrum: 470 $(M+1)^+$ $R_f$ value: 0.58 (silica gel; methylene chloride/methanol=9:1)

The following compounds are obtained analogously:
(1) 6-[4-[N-(ethoxycarbonyl)-amidino]-phenyl]-4-[[trans-4-(methoxycarbonyl)-cyclohexyl]-aminocarbonyl]-2-methyl-(2H)-pyridazin-3-one
Ethyl chloroformate is used.
Mass spectrum: 483 $M^+$ $R_f$ value: 0.54 (silica gel; methylene chloride/methanol=9:1)
(2) 6-[4-[N-(methoxycarbonyl)-amidino]-phenyl]-4-[[cis-4-(methoxycarbonyl)-cyclohexyl]-aminocarbonyl]-2-methyl-(2H )-pyridazin-3-one
Mass spectrum: 469 $M^+$ $R_f$ value: 0.73 (silica gel; methylene chloride/methanol=9:1)
(3) 4-methoxy-2-[4-[N-(methoxycarbonyl)-amidino]-phenyl]-5-[4-[(methoxycarbonyl)-methyl]-piperidinocarbonyl]-pyrimidine
Melting point: 193°–195° C., Mass spectrum: 469 $M^+$ $R_f$ value: 0.48 (silica gel; methylene chloride/methanol=9:1)
(4) 5-[4-[N-(methoxycarbonyl)-amidino]-phenyl]-2-[4-[(methoxycarbonyl)-methyl]-piperidinocarbonyl]-pyrimidine
(5) 4-[N-[trans-4-(benzyloxycarbonyl)-cyclohexyl]-N-methylaminocarbonyl]-6-[4-[N-(methoxycarbonyl)-amidino]-phenyl]- 2-methyl-(2H)-pyridazin-3-one
The benzylester is used as starting compound.
(6) 6-[4-[N-methoxycarbonyl)-amidino]-phenyl]-4-[[trans-4-(methoxycarbonyl)-cyclohexyl]-aminocarbonyl]-2-[(morpholinocarbonyl)-methyl]-(2H)-pyridazin-3-one (7) 6-[4-[[(N-acetyloxymethyl)-oxycarbonyl]-amidino]-phenyl]-4-[[trans-4-(methoxycarbonyl)-cyclohexyl]-aminocarbonyl]-2-[(morpholinocarbonyl)-methyl]-(2H)-pyridazin-3-one Acetyloxymethyl-(4-nitrophenyl)-carbonate and N-ethyl-diisopropylamine are used.

(8) 6-[4-[[(1-acetyloxy-ethyl)-oxycarbonyl]-amidino]-phenyl]-4-[[trans-4-(ethoxycarbonyl)-cyclohexyl]-aminocarbonyl]-2-[(morpholinocarbonyl)-methyl]-(2H)-pyridazin-3-one (1-acetyloxy-ethyl)-(4-nitrophenyl)-carbonate and N-ethyl-diisopropylamine are used.

(9) 2-[4-[N-(methoxycarbonyl)-amidino]-phenyl]-5-[N-[trans-4-(methoxycarbonyl)-cyclohexyl]-N-methyl-aminocarbonyl]-pyrimidine

(10) 2-[4-[(diethylphosphono)-amidino]-phenyl]-5-[N-[trans-4-(methoxycarbonyl)-cyclohexyl]-N-methyl-aminocarbonyl]-pyrimidine The reaction is carried out with diethylphosphate chloride in tetrahydrofuran/water with the dropwise addition of sodium hydroxide solution followed by chromatographic purification.

EXAMPLE 4

6-[4-(Aminomethyl)-phenyl]-4-[(trans-4-carboxy-cyclohexyl)-aminocarbonyl]-2-methyl-(2H)-pyridazin-3-one-hydrochloride A suspension of 1.50 g of 4-[(trans-4-carboxycyclohexyl)-aminocarbonyl]-6-(4-cyanophenyl)-2-methyl-(2H)-pyridazin-3-one and 0.5 g of Raney nickel in 500 ml of concentrated ammoniacal methanol is hydrogenated for 4½ hours at ambient temperature under a hydrogen pressure of 5 bar. The catalyst is filtered off and the filtrate is evaporated down using a rotary evaporator. The solids remaining are chromatographed over silica gel. 1.0 g (66% of theory) of product are obtained. In order to prepare the hydrochloride 310 mg of the product are suspended in 150 ml of tetrahydrofuran. Ethereal hydrochloric acid is added dropwise thereto, followed by sufficient water to form a solution. The organic solvents are evaporated off. The precipitate is suction filtered, washed with a little water and dried at 80° C.

Yield: 290 mg (56% of theory), Melting point: sintering from 287° C. Mass spectrum: 384 M$^+$ R$_f$ value: 0.57 (silica gel; methylene chloride/methanol/conc. ammonia solution=4:1:0.25)

| Calc.: × HCl × H$_2$O: | C 54.73 | H 6.20 | N 12.76 | Cl 8.08 |
| --- | --- | --- | --- | --- |
| Found: | 54.67 | 6.06 | 12.66 | 7.96 |

The following compounds are obtained analogously:
(1) 6-[4-(aminomethyl)-phenyl]-2-benzyl-4-[(trans-4-carboxycyclohexyl)-aminocarbonyl]-(2H)-pyridazin-3-one-hydrochloride Mass spectrum: 460 M$^+$ R$_f$ value: 0.62 (silica gel; methylene chloride/methanol/conc. ammonia solution=2:1:0.25)
(2) 5-aminomethyl-2-[4-[4-(carboxymethyl)-piperidino-carbonyl]-phenyl]-pyridine

EXAMPLE 5

6-[4-(Aminomethyl)-phenyl]-4-[[trans-4-(methoxycarbonyl)-cyclohexyl]-aminocarbonyl]-2-methyl-(2H)-pyridazin-3-one-hydrochloride A solution of 780 mg of 6-[4-(aminomethyl)-phenyl]-4-[(trans-4-carboxycyclohexyl)-aminocarbonyl]-2-methyl-(2H)-pyridazin-2-one in a mixture of 400 ml of absolute methanol and 50 ml of ethereal hydrochloric acid is stirred for 16 hours at ambient temperature. The solvent is evaporated off and the residue is chromatographed over silica gel.

Yield: 440 mg (50% of theory), Melting point: 175°–178° C. Mass spectrum: 398 M$^+$ R$_f$ value: 0.28 (silica gel; methylene chloride/methanol=9:1)

The following compounds are obtained analogously:
(1) 6-[4-(aminomethyl)-phenyl]-2-benzyl-4-[[trans-4-(methoxycarbonyl)-cyclohexyl]-aminocarbonyl]-(2H)-pyridazin-3-one-hydrochloride Mass spectrum: 474 M$^+$ R$_f$ value: 0.64 (silica gel; methylene chloride/methanol/conc. ammonia solution=8:1:0.1)
(2) 5-aminomethyl-2-[4-4-[(methoxycarbonyl)-methyl]-piperidinocarbonyl]-phenyl]-pyridine-hydrochloride

EXAMPLE 6

2-[4-[N-(Benzyloxycarbonyl)-amidino]-phenyl]-5-[4-[(benzyloxycarbonyl)-methyl]-4-hydroxy-piperidinocarbonyl]-pyrimidine Prepared by reacting 2-[4-[N-(benzyloxycarbonyl)-amidino]-phenyl]-5-carboxy-pyrimidine with 1.2 equivalents of N,N-carbonyl-diimidazole in dimethylformamide at 5° C. followed by the addition of 1.2 equivalents of 4-[(benzyloxycarbonyl)-methyl]-4-hydroxy-piperidine-hydrochloride and 1.2 equivalents of N-methylmorpholine at ambient temperature.

EXAMPLE 7

2-(4-Amidinophenyl)-5-[4-(carboxymethyl)-4-hydroxypiperidinocarbonyl]-pyrimidine Prepared by hydrogenation of 2-[4-[N-(benzyloxycarbonyl)-amidino]-phenyl]-5-[4-[(benzyloxycarbonyl)-methyl]-4-hydroxy-piperidino-carbonyl]-pyrimidine in methanol in the presence of 10% palladium on charcoal at ambient temperature under a hydrogen pressure of 5 bar.

The following compound is obtained analogously:
(1) 4-[N-(trans-4-carboxy-cyclohexyl )-N-methyl-aminocarbonyl]-6-[4-[N-(methoxycarbonyl)-amidino]-phenyl]-2-methyl-2H-pyridazin-3-one

EXAMPLE 8

2-(4-Amidinophenyl)-5-[4-[[(pyridin-3-ylmethyl)-oxycarbonyl]-methyl]-piperidinocarbonyl]-pyrimidine 2-(4-amidinophenyl)-5-[4-(carboxymethyl)-piperidinocarbonyl]-pyrimidine is esterified with a 12-fold excess of 3-hydroxymethyl-pyridine and a 15-fold excess of methanesulphonic acid in dimethylformamide.

The following compound is obtained analogously:
(1) 6-(4-amidinophenyl)-4-[N-[trans-4-(benzyloxy-carbonyl)-cyclohexyl]-N-methyl-aminocarbonyl]-2-methyl-(2H)-pyridazin-3-one-toluenesulphonate The work is done in benzyl alcohol as solvent using 2 equivalents of toluenesulphonic acid.

EXAMPLE 9

6-(4-Amidinophenyl)-2-benzyl-4-[[trans-4-(isopropoxy-carbonyl)-cyclohexyl]-aminocarbonyl]-(2H)-pyridazin-3-one A solution of 130 mg of 6-(4-aminophenyl)-2-benzyl-4-[(trans-4-(carboxycyclohexyl)-aminocarbonyl]-(2H)-pyridazin-3-one in 30 ml of isopropanol saturated with hydrogen chloride is stirred for 30 hours at ambient temperature. The solvent is evaporated down under reduced pressure and the residue is chromatographed over silica gel.

Yield: 40 mg (20% of theory), Mass spectrum: 516 $(M+H)^+$ $R_f$ value: 0.12 (silica gel; methylene chloride/isopropanol/conc. ammonia solution=4:1:0.25)

The following compounds are obtained analogously:

(1) 6-(4-amidinophenyl)-4-[[trans-4-(cyclohexyloxy-carbonyl)-cyclohexyl]-aminocarbonyl]-2-[(morpholino-carbonyl)-methyl]-(2H)-pyridazin- 3-one The reaction is carried out in a mixture of cyclohexanol/methylene chloride saturated with hydrogen chloride.

(2) 6-(4-amidinophenyl)-4-[[trans-4-(cyclohexyl-methyloxycarbonyl)-cyclohexyl]-aminocarbonyl]-2-[(morpholinocarbonyl)-methyl]-(2H)-pyridazin-3-one The reaction is carried out in a mixture of cyclohexylmethanol/methylene chloride saturated with hydrogen chloride.

(3) 6-(4-amidinophenyl)-4-[[trans-4-(ethoxycarbonyl )-cyclohexyl]-aminocarbonyl]-2-[(morpholinocarbonyl)-methyl]-(2H)-pyridazin-3-one The reaction is carried out in ethanol saturated with hydrogen chloride.

(4) 2-(4-amidinophenyl)-5-[N-methyl-N-[trans-4-(isopropoxycarbonyl)-cyclohexyl]-aminocarbonyl]-pyrimidine (5) 2-(4-amidinophenyl)-5-[N-[trans-4-(cyclohexyloxy-carbonyl)-cyclohexyl]-N-methyl-aminocarbonyl]-pyrimidine The reaction is carried out in a mixture of cyclohexanol/methylene chloride saturated with hydrogen chloride.

(6) 2-(4-amidinophenyl)-5-[N-[trans-4-(cyclopentyl-methoxycarbonyl)-cyclohexyl]-N-methyl-aminocarbonyl]-pyrimidine The reaction is carried out in a mixture of cyclopentylmethanol/methylene chloride saturated with hydrogen chloride.

EXAMPLE 10

2-[4-(Aminomethyl)-phenyl]-5-[4-[(methoxycarbonyl)-methyl]-piperidinocarbonyl]-(3H)-pyrimidin-4-one-hydrochloride A suspension of 670 mg of 2-(4-cyanophenyl)-5-[4-[(methoxycarbonyl)-methyl]-piperidinocarbonyl]-(3H)-pyrimidin-4-one and 100 mg of 10% palladium on charcoal in 125 ml of methanol and 20 ml of ethereal hydrochloric acid is hydrogenated for 3 hours at ambient temperature under a hydrogen pressure of 3 bar. The catalyst is filtered off and the filtrate is evaporated down under reduced pressure. The solids remaining are triturated with ether and suction filtered.

Yield: 740 mg (100% of theory), Melting point: 205° C. (decomp.) $R_f$ value: 0.18 (silica gel; methylene chloride/methanol/conc. ammonia solution=4:1:0.25)

EXAMPLE 11

Dry ampoule containing 2.5 mg of active substance per 1 ml

Composition:

| Active substance | 2.5 mg |
|---|---|
| Mannitol | 50.0 mg |
| Water for injections ad | 1.0 ml |

Preparation:

The active substance and mannitol are dissolved in water. After packaging, the ampoules are freeze-dried.

The solution ready for use is made up with water for injections.

EXAMPLE 12

Dry ampoule containing 35 mg of active substance per 2 ml

Composition:

| Active substance | 35.0 mg |
|---|---|
| Mannitol | 100.0 mg |
| Water for injections ad | 2.0 ml |

Preparation:

The active substance and mannitol are dissolved in water. After packaging, the ampoules are freeze-dried.

The solution ready for use is made up with water for injections.

EXAMPLE 13

Tablet containing 50 mg of active substance

Composition:

| (1) Active substance | 50.0 mg |
|---|---|
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granules. From this mixture, compressed tablets are made, which are biplanar, facetted on both sides and notched on one side. Diameter of tablets: 9 mm.

EXAMPLE 14

Tablet containing 350 mg of active substance

Composition:

| (1) Active substance | 350.0 mg |
|---|---|
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granules. From this mixture, compressed tablets are made, which are biplanar, facetted on both sides and notched on one side. Diameter of tablets: 12 mm.

EXAMPLE 15

Capsules containing 50 mg of active substance

41

Composition:

| | | |
|---|---|---|
| (1) Active substance | 50.0 mg | |
| (2) Dried corn starch | 58.0 mg | |
| (3) Powdered lactose | 50.0 mg | |
| (4) Magnesium stearate | 2.0 mg | |
| | 160.0 mg | |

Preparation:

(1) is triturated with (3). This trituration is added to the mixture of (2) and (4) with thorough mixing.

The powdered mixture is packed into hard gelatin oblong capsules, size 3, in a capsule filling machine.

EXAMPLE 16

Capsule containing 350 mg of active substance
Composition:

| | | |
|---|---|---|
| (1) Active substance | 350.0 mg | |
| (2) Dried corn starch | 46.0 mg | |
| (3) Powdered lactose | 30.0 mg | |
| (4) Magnesium stearate | 4.0 mg | |
| | 430.0 mg | |

Preparation:

(1) is triturated with (3). This trituration is added to the mixture of (2) and (4) with thorough mixing.

The powdered mixture is packed into hard gelatin oblong capsules, size 0, in a capsule filling machine.

What is claimed is:

1. A heterobiaryl derivative of the formula

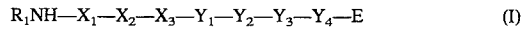

$$R_1NH-X_1-X_2-X_3-Y_1-Y_2-Y_3-Y_4-E \quad (I)$$

wherein $R_1$ denotes a hydrogen atom, a $C_{1-4}$-alkyl, group or an alkoxycarbonyl group having a total of 2 to 5 carbon atoms optionally phenyl-substituted in the alkoxy moiety, a phosphono group, an O-alkyl-phosphono or dialkylphosphoryl group wherein each alkyl moiety contains 1 or 2 carbon atoms, or an R'—CO—O—(R"CH)—O—CO— group, wherein R' represents a $C_{1-4}$-alkyl group, or a $C_{5-6}$-cycloalkyl group and R" denotes a hydrogen atom or a methyl group, $X_1$ represents a $C_{1-2}$alkylene group, or —C(=NH)— group, $X_2$ represents a phenylene, group, or a phenylene group substituted by a fluorine, chlorine, or bromine atom or by a $C_1$–$C_2$ alkyl, amino, hydroxy or $C_1$–$C_2$ alkoxy group $X_3$ represents a pyridinylene, pyrazinylene, pyrimidinylene or pyridazinylene group each optionally substituted in the carbon skeleton by a fluorine, chlorine or bromine atom or by a $C_1$–$C_2$ alkyl, amino, hydroxy or $C_1$–$C_2$ alkoxy group, $Y_1$ represents a bond, $Y_2$ represents a bond, $Y_3$ represents a 1,4-piperazinylene group, $Y_4$ represents a straight chained or branched $C_{1-4}$-alkylene group, and

42

E represents a sulpho, 5-tetrazolyl, phosphono, O-methylphosphono, R'—CO—O—(R"CH)—O—CO—, R'''CO— or R'O—CO—O—(R"CH)—O—CO— group, wherein R' and R" are as hereinbefore defined and R''' denotes a hydroxy group, a $C_{1-5}$-alkoxy group in which the alkoxy moiety may be substituted in the 1-, or 2- position by a phenyl or pyridyl group or in the 2- or 3-position by a pyrrolidino, piperidino, hexamethyleneimino, morpholino or thiomorpholino group, a $C_{4-7}$-cycloalkoxy group, a cycloalkylalkoxy group having 4 to 7 carbon atoms in the cycloalkyl moiety and 1 to 3 carbon atoms in the alkoxy moiety, or a phenylallyloxy group, a tautomer, stereoisomer and mixture thereof or a salt thereof.

2. A heterobiaryl derivative as recited in claim 1 wherein $R_1$ represents a hydrogen atom, a $C_{1-4}$-alkyl group, an alkoxycarbonyl group having a total of 2 to 5 carbon atoms, a benzyloxycarbonyl, dimethylphosphoryl, diethylphosphoryl or R'—CO—O—(R"CH)—O—CO— group, wherein R' represents a methyl or ethyl group and R" represents a hydrogen atom or a methyl group, $X_1$ represents a methylene group or a —C(=NH)— group, $X_2$ represents a phenylene, group or a phenylene group substituted by a fluorine, chlorine or bromine or by a methyl, hydroxy, methoxy, ethoxy, amino or dimethylamino group, $X_3$ represents a pyridinylene, pyrazinylene, pyrimidinylene or pyridazinylene group each of which may be substituted in the carbon skeleton by a fluorine, chlorine or bromine or by a methyl, hydroxy, methoxy, ethoxy, amino or dimethylamino group, $Y_1$ represents a bond, $Y_2$ represents a bond, $Y_3$ represents a 1,4-piperazinylene group, $Y_4$ represents a straight-chained or branched $C_{1-4}$-alkylene group, and E represents R'''CO— group, wherein R''' represents a hydroxy group, a $C_{1-4}$-alkoxy group, a cycloalkoxy or cycloalkoxymethoxy group, each having 5 or 6 carbon atoms in the cycloalkoxy moiety or a benzyloxy or pyridylmethoxy group, a tautomer, stereoisomer or mixtures thereof, or a salt thereof.

3. A heterobiaryl derivative as recited in claim 1, wherein $R_1$ represents a hydrogen atom, or a alkoxycarbonyl group with a total of 2 or 3 carbon atoms, $X_1$ represents a methylene group or a —C(=NH)— group, $X_2$ represents a phenylene, group or a phenylene group substituted by a fluorine, chlorine or bromine or by a methyl or methoxy group, $X_3$ represents a pyridinylene, pyrazinylene, pyrimidinylene or pyridazinylene group each of which may be substituted in the carbon skeleton by a fluorine, chlorine or bromine or by a methyl or methoxy group, $Y_1$ represents a bond, $Y_2$ represents a bond, $Y_3$ represents a 1,4-piperazinylene, $Y_4$ represents an alkylene group having 1 or 2 carbon atoms, and E represents a carboxy group or an alkoxycarbonyl group having a total of 2 to 4 carbon atoms, a tautomer, stereoisomer or mixtures thereof, or a salt thereof.

4. A heterobiaryl derivative as recited in claim 1 wherein $R_1$ represents a hydrogen atom or an alkoxycarbonyl group with a total of 2 or 3 carbon atoms, $X_1$ represents a methylene group or a —C(=NH)— group, $X_2$ represents a phenylene group, or phenylene group substituted by a fluorine, chlorine or bromine or by a methyl or methoxy group, $X_3$ represents a pyridazinylene, pyrimidinylene or pyridazinylene group each of which may be substituted in the carbon skeleton by a fluorine, chlorine or bromine or by a methyl or methoxy group, $Y_1$ represents a bond, $Y_2$ represents a bond, $Y_3$ represents a 1,4-piperazinylene group, $Y_4$ represents an alkylene group having 1 or 2 carbon atoms, and E represents a carboxy group or an alkoxycarbonyl group having a total of 2 to 4 carbon atoms, a tautomer, stereoisomer or mixtures thereof, or a salt thereof.

5. A heterobiaryl derivative as recited in claim 1, wherein $R_1$ represents a hydrogen atom or an alkoxycarbonyl group having a total of 2 or 3 carbon atoms, $X_1$ represents a methylene group or a —C(=NH)— group, $X_2$ represents a phenylene group, or a phenylene group substituted by a fluorine, chlorine or bromine or by a methyl or methoxy group, $X_3$ represents a pyrimidinylene or pyridazinylene group, $Y_1$ represents a bond, $Y_2$ represents a bond, $Y_3$ represents a 1,4-piperazinylene group, $Y_4$ represents a methylene group or ethylene group, and E is a carboxy group or an alkoxycarbonyl group with a total of 2 or 3 carbon atoms, a tautomer, stereoisomer or mixtures thereof, or a salt thereof.

6. A heterobiaryl derivative as recited in claim 1, wherein $R_1$ represents a hydrogen atom or an alkoxycarbonyl group having a total of 2 or 3 carbon atoms, $X_1$ represents a methylene group or a —C(=NH)— group, $X_2$ represents a phenylene group, $X_3$ represents a pyrimidinylene or pyridazinylene group, $Y_1$ represents a bond, $Y_2$ represents a bond, $Y_3$ represents a 1,4-piperazinylene group, $Y_4$ represents a methylene or ethylene group, and E represetns a carboxy group or an alkoxycarbonyl group with a total or 2 or 3 carbon atoms, a tautomer, stereoisomer or mixtures thereof, or a salt thereof.

7. 6-(4-amidinophenyl)-3-[4-(carboxymethyl)-piperazino]-pyridazine or a salt thereof.

* * * * *